US006429187B1

(12) United States Patent
Sontheimer et al.

(10) Patent No.: US 6,429,187 B1
(45) Date of Patent: *Aug. 6, 2002

(54) METHOD OF DIAGNOSING AND TREATING GLIOMAS

(75) Inventors: Harald W. Sontheimer, Birmingham, AL (US); Nicole Ullrich, Fairfield, CT (US)

(73) Assignee: UAB Research Foundation, Birmingham, AL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/980,395

(22) Filed: Nov. 28, 1997

Related U.S. Application Data

(62) Division of application No. 08/774,154, filed on Dec. 26, 1996, now Pat. No. 5,905,027.
(60) Provisional application No. 60/009,283, filed on Dec. 27, 1995.

(51) Int. Cl.[7] .............................................. A61K 38/00
(52) U.S. Cl. ........................ 514/2; 530/350; 424/130.1; 424/1.49
(58) Field of Search ....................... 435/7.23; 424/1.11, 424/1.41, 1.49, 130.1; 514/2; 530/350

(56) References Cited

U.S. PATENT DOCUMENTS

| | | | |
|---|---|---|---|
| 5,212,290 A | | 5/1993 | Vogelstein et al. ........ 530/387.7 |
| 5,223,253 A | * | 6/1993 | Hall et al. ..................... 424/88 |
| 5,626,862 A | | 5/1997 | Brem et al. ................. 424/426 |
| 5,750,376 A | * | 5/1998 | Weiss et al. |
| 5,756,340 A | * | 5/1998 | Hammock et al. |
| 6,028,174 A | * | 2/2000 | Ullrich et al. .............. 530/350 |

OTHER PUBLICATIONS

Debin et al. Am. J. Physiol. 264, C361–C369, 1993.*
Hosli et al. Exp. Brain Res., 80 621–625, 1990.*
Ullrich et al. NeruoReport. 7, 1020–1024, Apr. 10, 1996.*
Phillips et al. Cancer Research. 54, 1008–1015, Feb. 15, 1994.*
DeBin et al. Am. J. Physio. Cell Physiol., 264, (2 Part 1), C361–C369, 1993.*
Malinowska et al. Biophysical J. 66 (2 Part 2) M–Pos 425, Mar. 1994.*
Baker, Effects of an epithelial Cl[−] channel blocker on whole cell voltage clamp and patch clamp recordings from a human astrocytoma in culture, J. Physiol. 438:128–129 (1991).
Brismar et al., Inward rectifying potassium channels in human malignant glioma cells, Brain Res. 480:249–258 (1989).

Brismar et al., Potassium and sodium channels in human malignant glioma cells, Brain Res. 480:259–267 (1989).
Chiu et al., The role of potassium channels in Schwann cell proliferation in Wallerian degeneration of explant rabbit sciatic nerves, J. Physiol. 408:199–222 (1989).
Deane et al., An alternative pathway of B cell activation: stilbene disulfonates interact with a Cl[−] binding motif on AEn–related proteins to stimulate motogenesis, Eur. J. Immunol. 22:1165–1171 (1992).
DeBin et al., Chloride channel inhibition by the venom of the scorpion *Leiurus quinquestriatus*, Toxicon. 29:1403–1408 (1991).
DeBin et al., Purification and characterization of cholortoxin, a chloride channel ligand from the venom of the scorpion, Am. J. Physiol. 264:C361–369 (1993).
De Muralt et al., Reactivity of antiglioma monoclonal antibodies for a large panel of cultured gliomas and other neuroectoderm derived tumors, Anticancer Res. 3:1–6 (1983).
Gray et al., A voltage–gated chloride conductance in rat cultured astrocytes, Proc. R. Soc. Lond. 228:267–288 (1986).
Grissmer et al., Calcium–activated potassium channels in resting and activated human T lymphocytes, J. Gen. Phys. 102:601–630 (1993).
Huang et al., Potassium channel induction by the Ras/Raf signal transduction cascade, J. Biol. Chem. 269:31183–31189 (1994).
Jalonen, Single–channel characteristics of the large–conductance anion channel in rat cortical astrocytes in primary culture, Glia 9:227–237 (1993).
Kunwar et al., Cytotoxicity and antitumor effects of growth factor–toxin fusion proteins on human glioblastoma multiforme cells, J. Neurosurg. 79:569–576 (1993).
Nilius et al., Potassium channels and regulation of proliferation of human melanoma cells, J. Physiol. 445:537–548 (1992).
Pappas et al., Reduction of glial proliferation by K[+] channel blockers is mediated by changes in $pH_1$, NeuroReport 6:193–196 (1994).
Pappone et al., Blockers of voltage–gated K channels inhibit proliferation of cultured brown fat cells, Am. J. Physiol. 264:C1014–1019 (1993).
Phillips et al., Transforming growth factor–α–pseudomonas exotoxin fusion protein (TGF–α–PE38) treatment of subcutaneous and intracranial human glioma and medulloblastoma xenografts in athymic mice, Cancer Research 54:1008–1015 (1994).

(List continued on next page.)

*Primary Examiner*—Sheela Huff
(74) *Attorney, Agent, or Firm*—Morgan, Lewis & Bockius LLP

(57) ABSTRACT

The present invention provides a recombinant toxin and monoclonal antibody which specifically binds to glial-derived or meningioma-derived tumor cells. Also provided are various methods of screening for malignant gliomas and meningiomas. Further provided are methods of treating malignant gliomas, including glioblastoma multiforme and astrocytomas.

9 Claims, 20 Drawing Sheets

OTHER PUBLICATIONS

Puro et al., Retinal glial cell proliferation and ion channels: A possible link, Invest. Ophthalmol. Vis. Sci. 30:521–529 (1989).

Sakamoto et al., Identification of a new outwardly rectifying Cl⁻ channel that belongs to a subfamily of the CIC Cl⁻ channels, J. Biol. Chem. 271:10210–102116 (1996).

Somogyi et al., Subcellular localization of benzodiazepine/ $GABA_A$ receptors in the cerebellum of rat, cat and monkey using monoclonal antibodies, J. Neurosci. 9:2197–2209 (1989).

Sontheimer, Voltage–dependent ion channels in glial cells, Glia 11:156–172 (1994).

Steinmeyer et al., Cloning and functional expression of rat CLC–5, a chloride channel related to kidney disease, J. Biol. Chem. 270:31172–31177 (1995).

Uchida et al., Localization and functional characterization of rat kidney–specific chloride channel CIC–K1, J. Clin. Invest. 95:104–113 (1995).

Ullrich et al., Human astrocytoma cells express a unique chloride current, NeuroReport 7:1020–1024 (1996).

Ullrich et al., Biophysical and pharmacological characterization of chloride currents in human astrocytoma cells, Am. J. Physiol. 270:C1511–1521 (1996).

Wilson et al., Mitogenic factors regulate ion channels in Schwann cells cultured from newborn rat sciatic nerve, J. Physiol. 470:501–520 (1993).

Woodfork et al., Inhibition of ATP–sensitive potassium channels causes reversible cell–cycle arrest of human breast cancer cells in tissue culture, J. Cell. Physiol. 162:163–171 (1995).

Uchida et al. J. Clin. Invest. 95, 104–113, Jan. 1995.*

Goldstein et al, Scientific American vol. 255 p. 74 1986.*

* cited by examiner

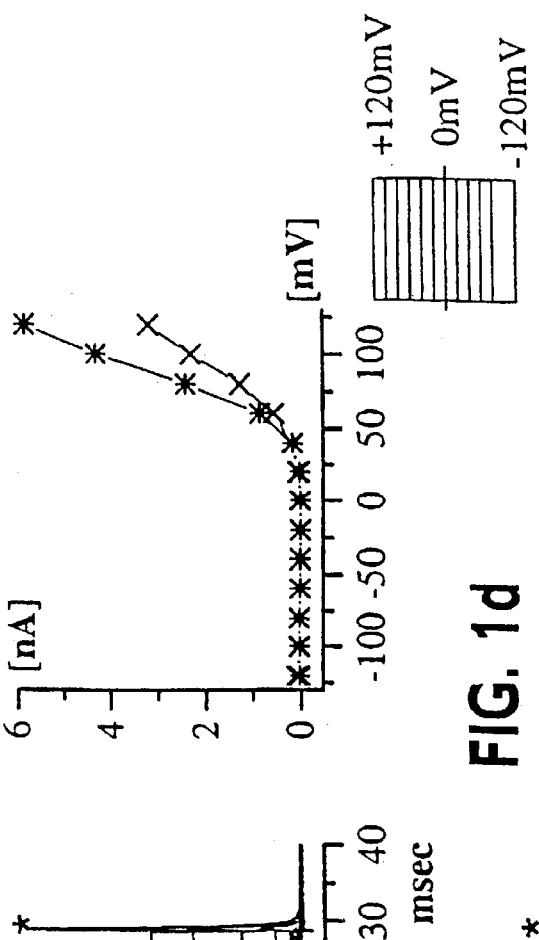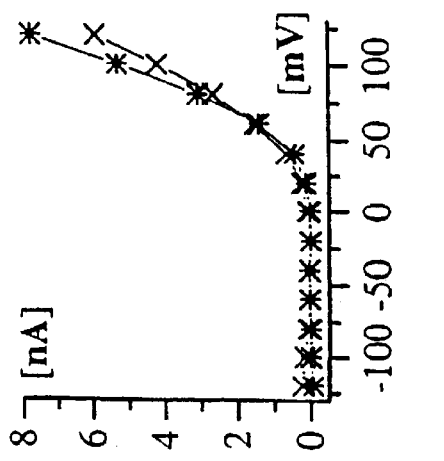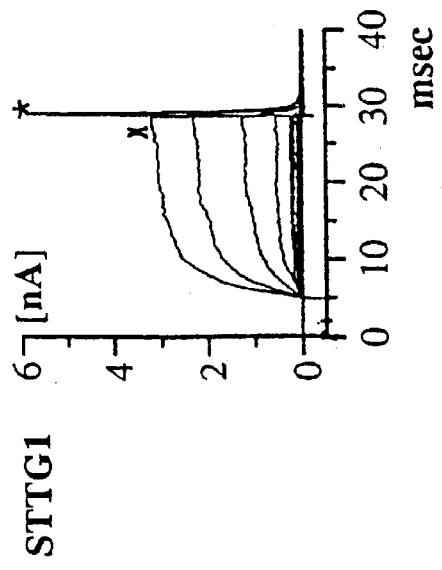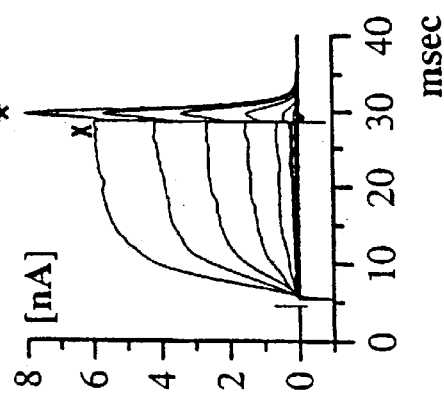
FIG. 1a STTG1
FIG. 1b
FIG. 1c UAB4630
FIG. 1d

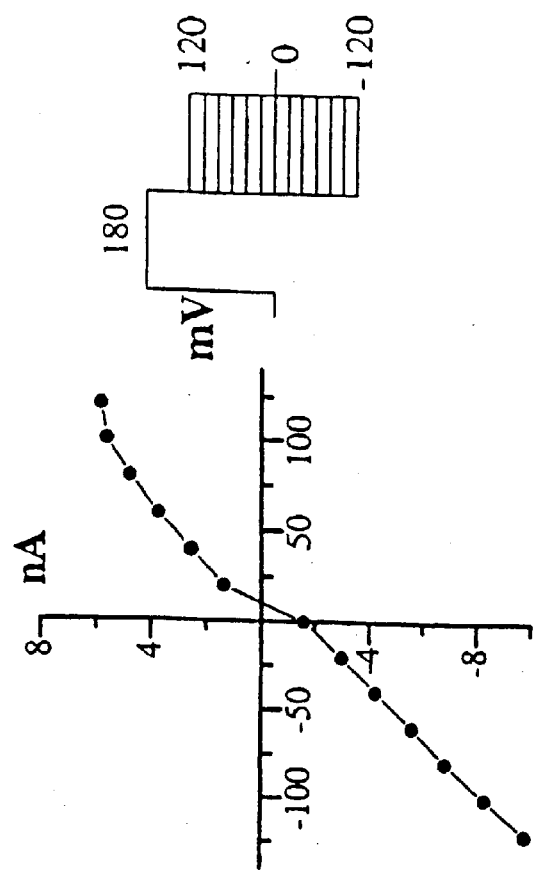
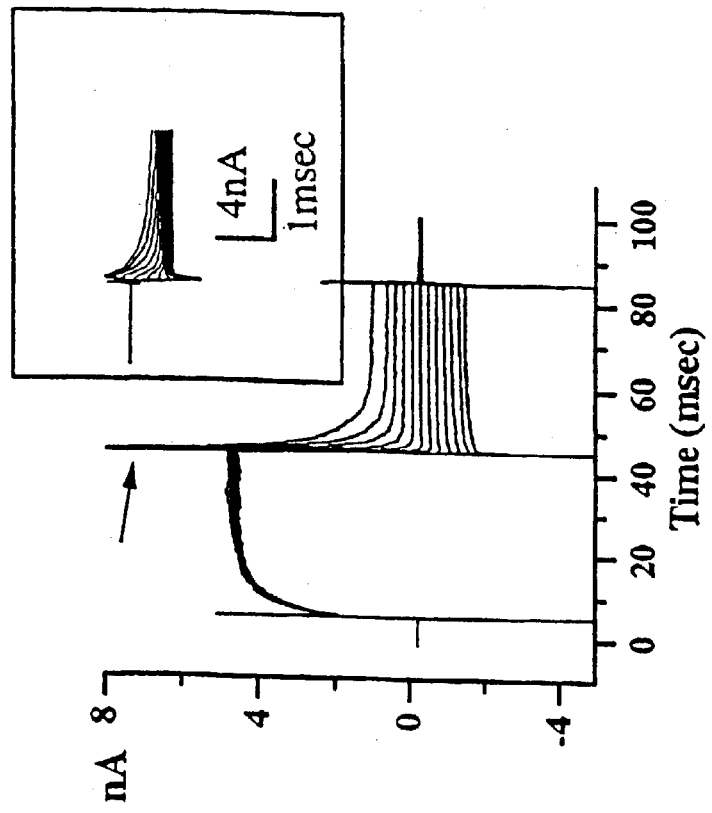
FIG. 2b
FIG. 2a

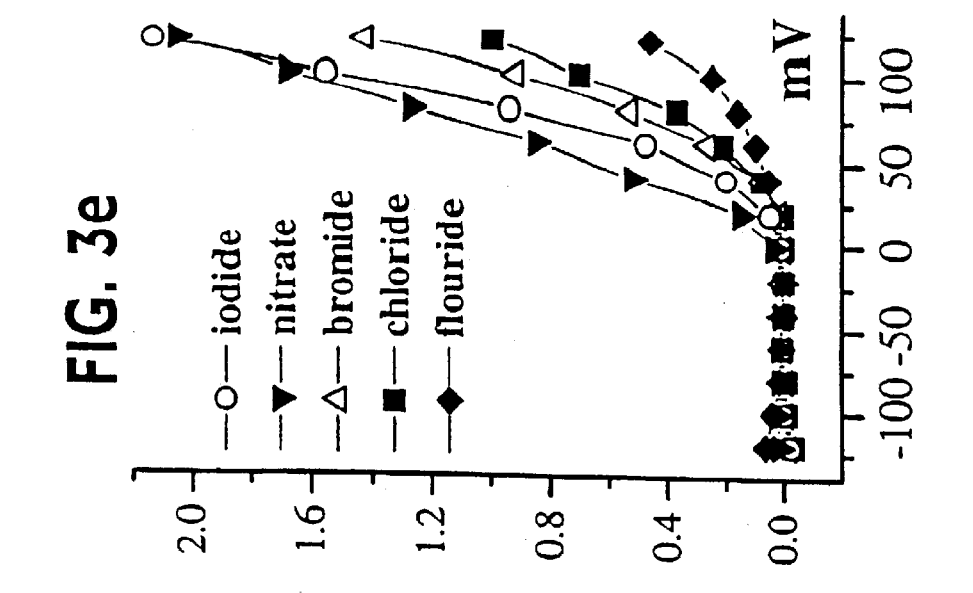
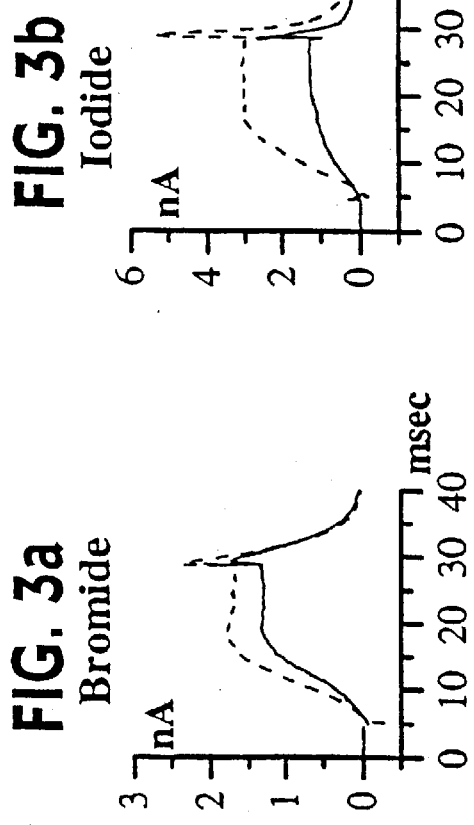
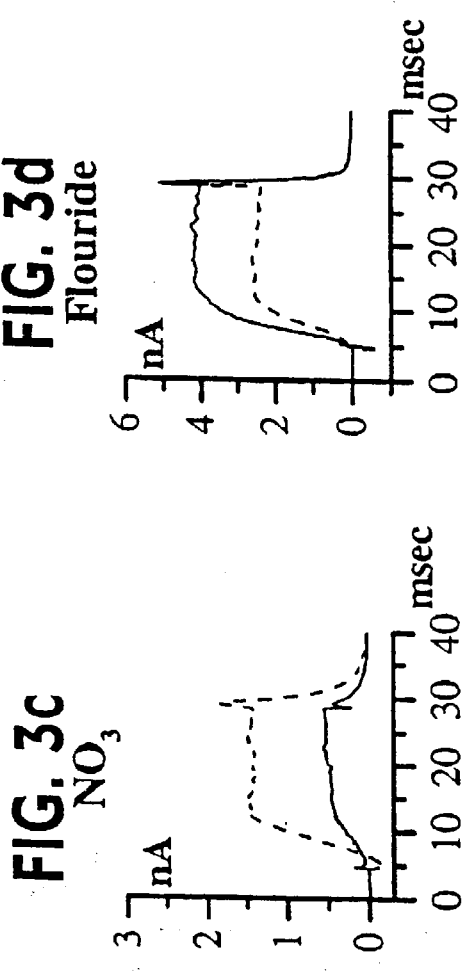

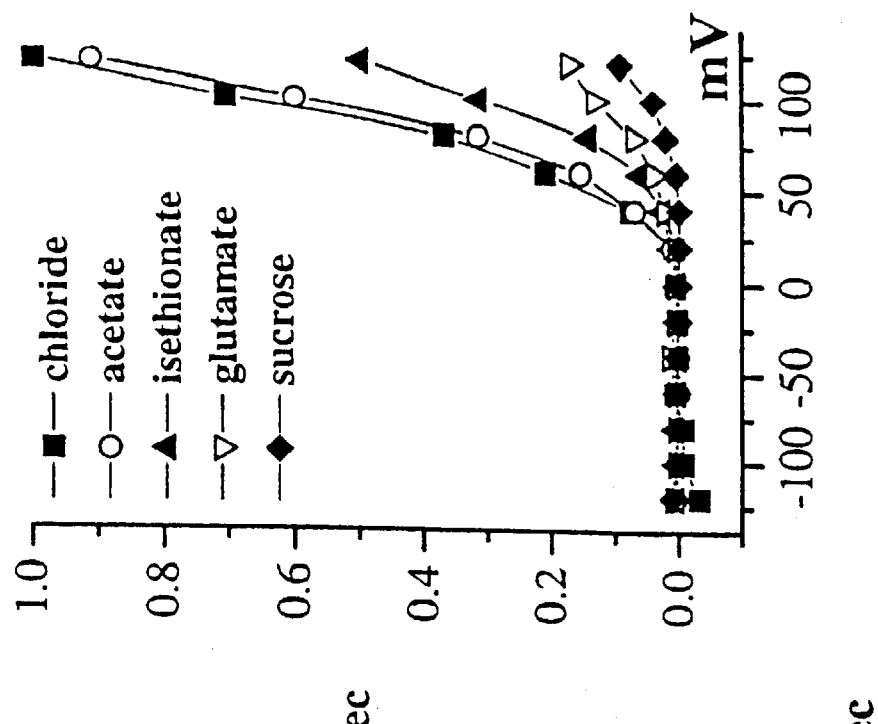
FIG. 4e
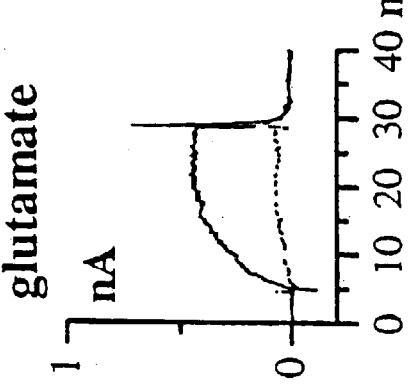
FIG. 4b glutamate
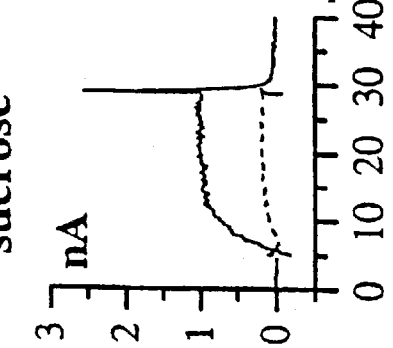
FIG. 4d sucrose
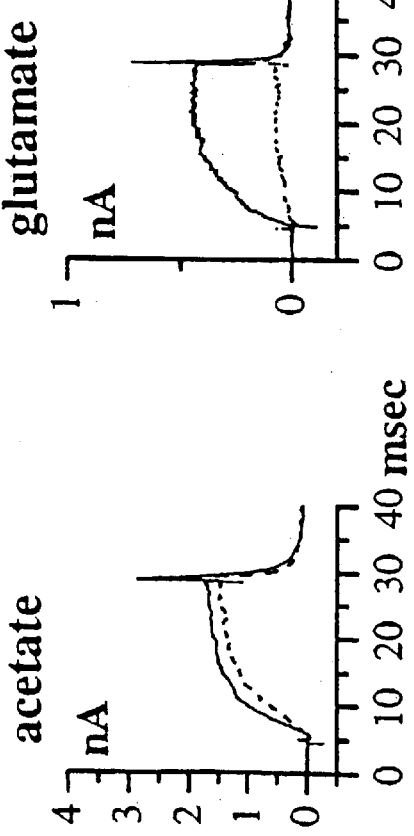
FIG. 4a acetate
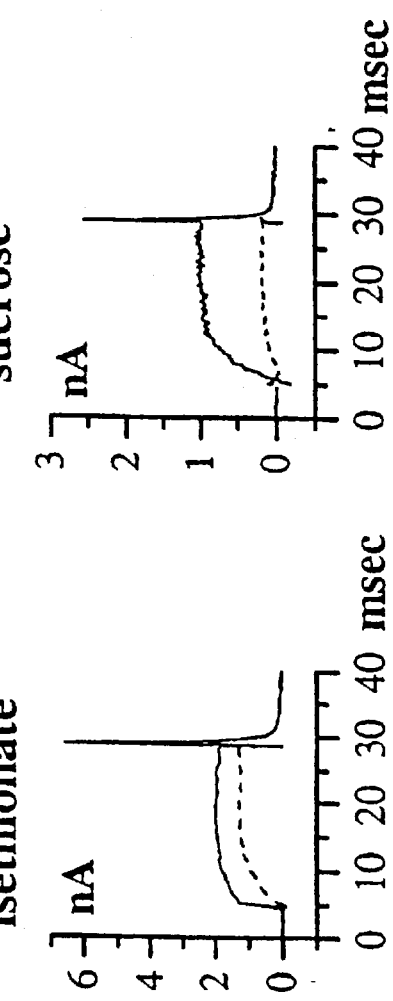
FIG. 4c isethionate

FIG. 5a control
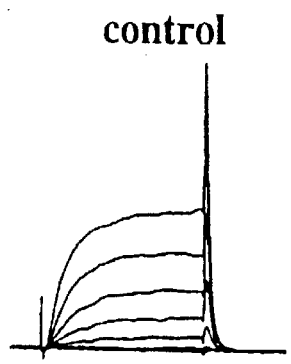
FIG. 5b chlorotoxin
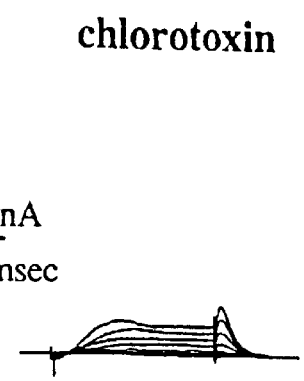
FIG. 5c
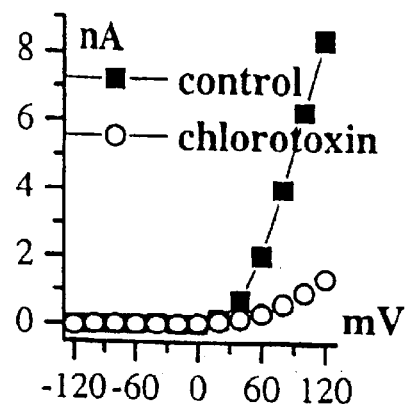
FIG. 5d ctrl
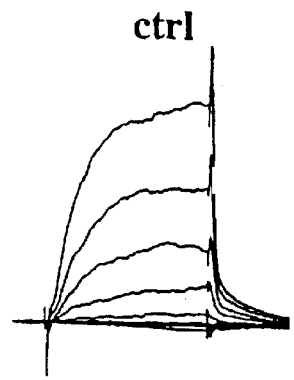
FIG. 5e DIDS
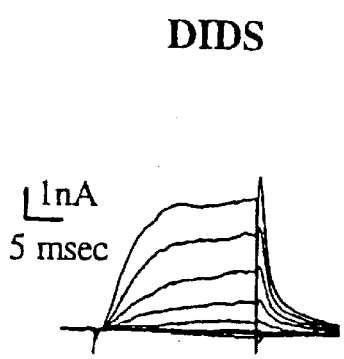
FIG. 5f
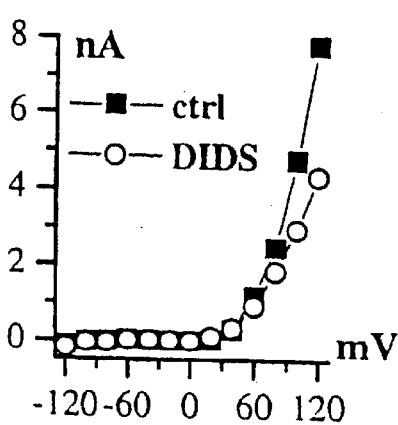
FIG. 5g ctrl   FIG. 5h DNDS
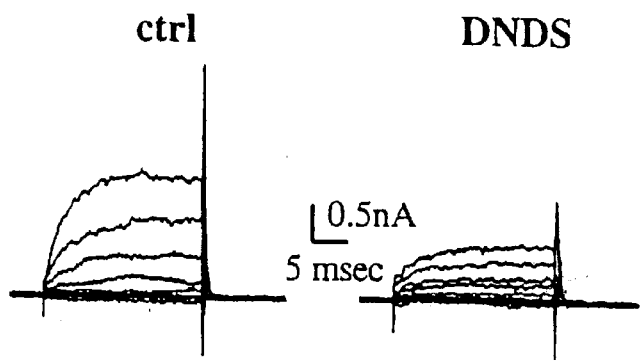
FIG. 5i
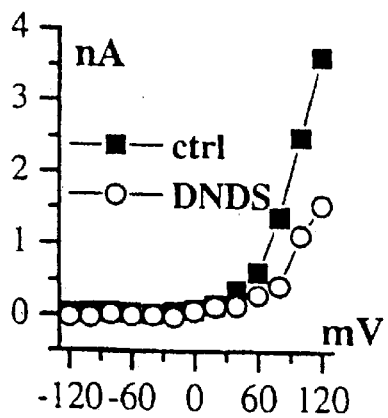

ctrl zinc 0.5nA
5msec ctrl cadmium 0.5nA
5msec ctrl 0 calcium

1nA
5 msec

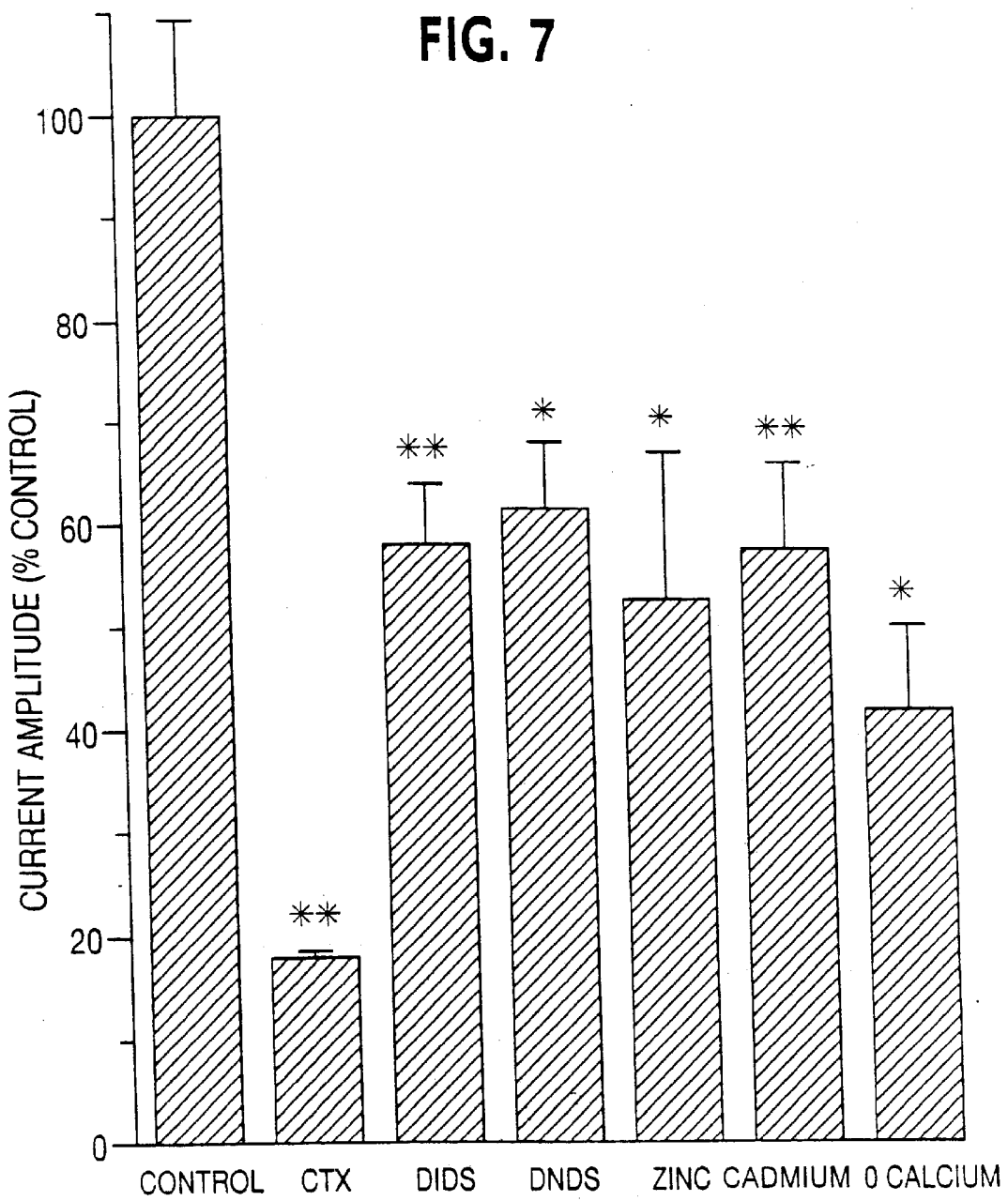

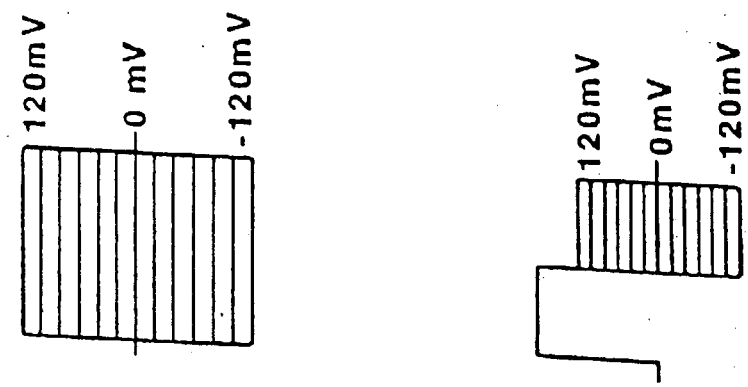
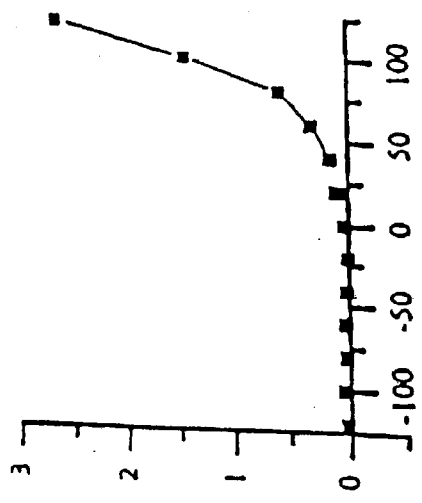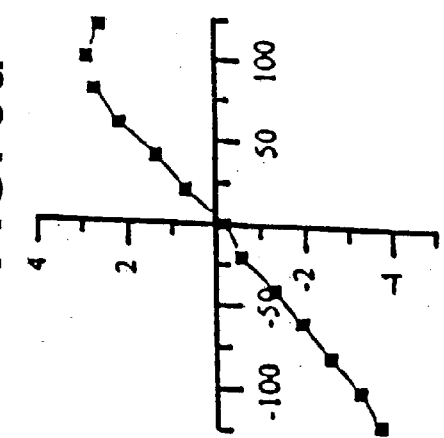
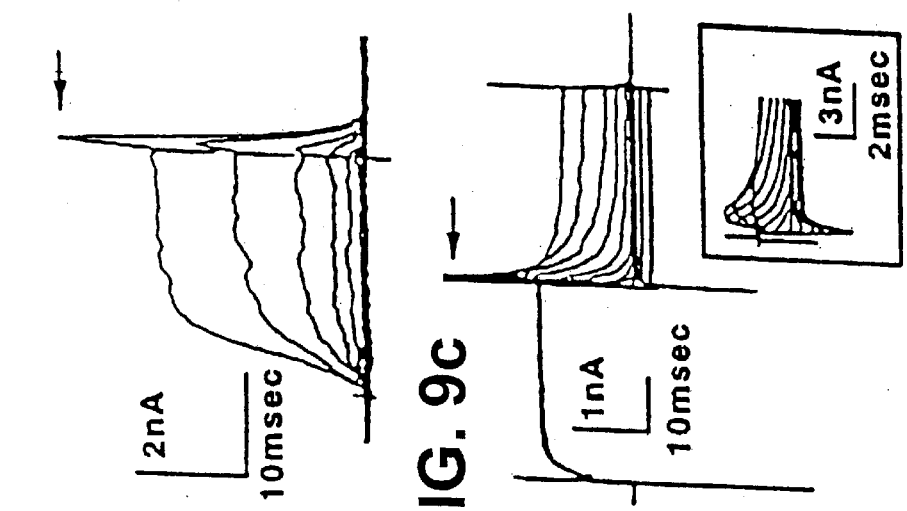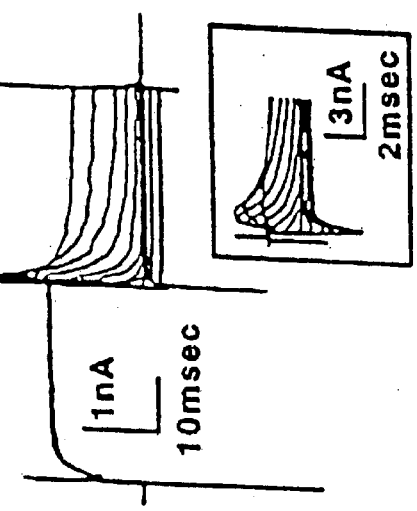
FIG. 9a  FIG. 9b  FIG. 9c  FIG. 9d

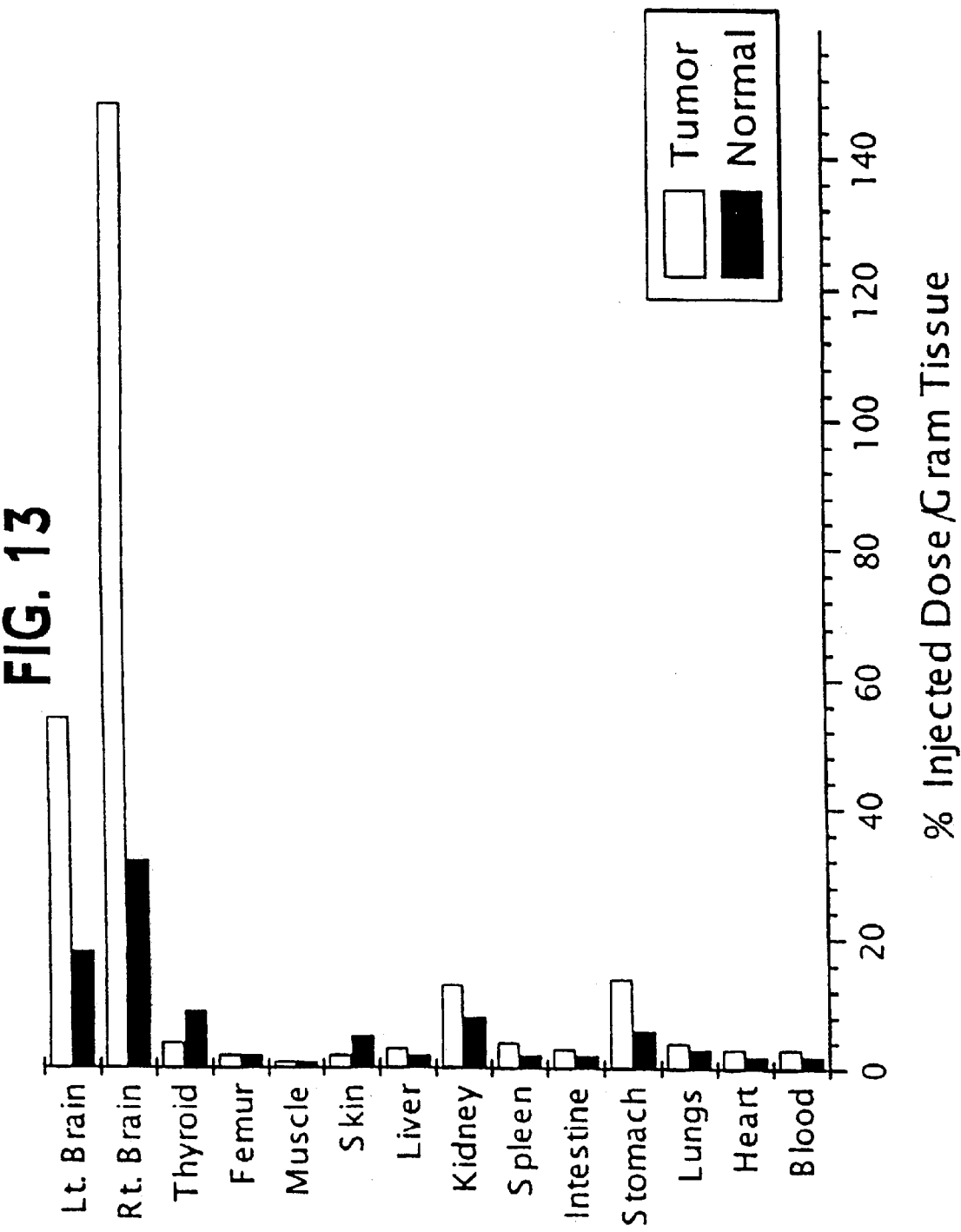

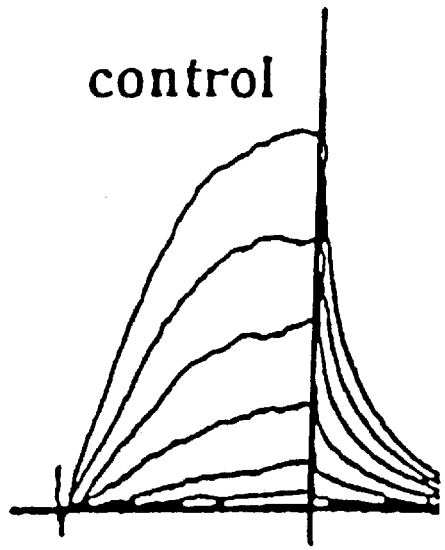
FIG. 14a control
FIG. 14b chlorotoxin
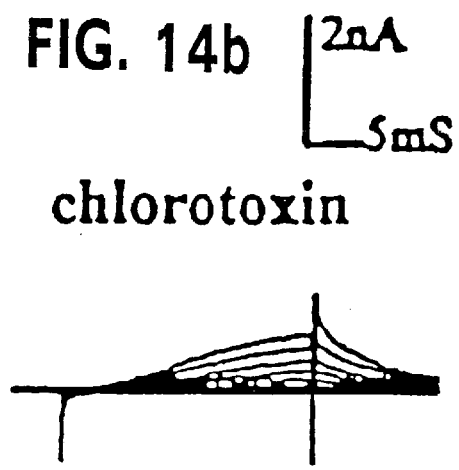
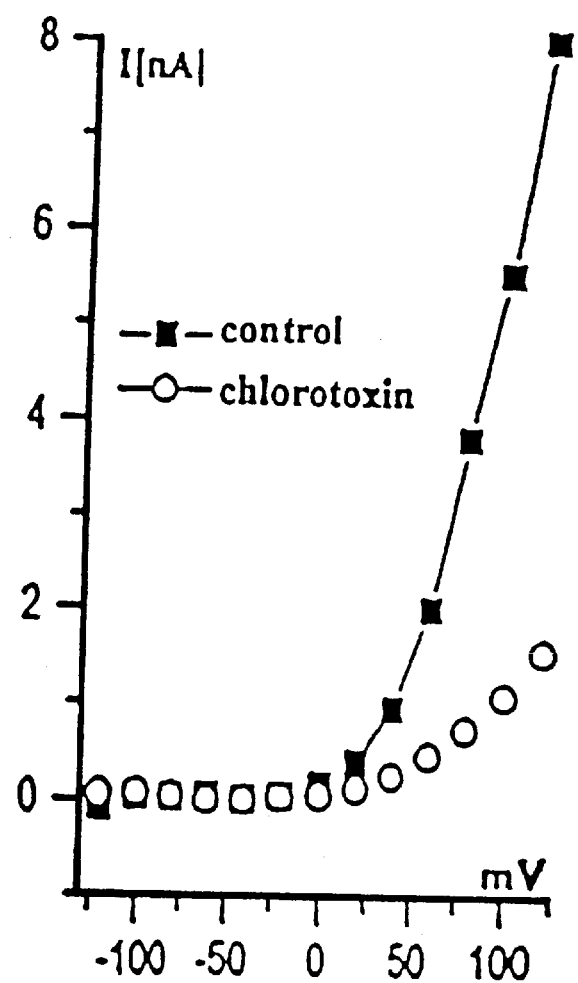
FIG. 14c

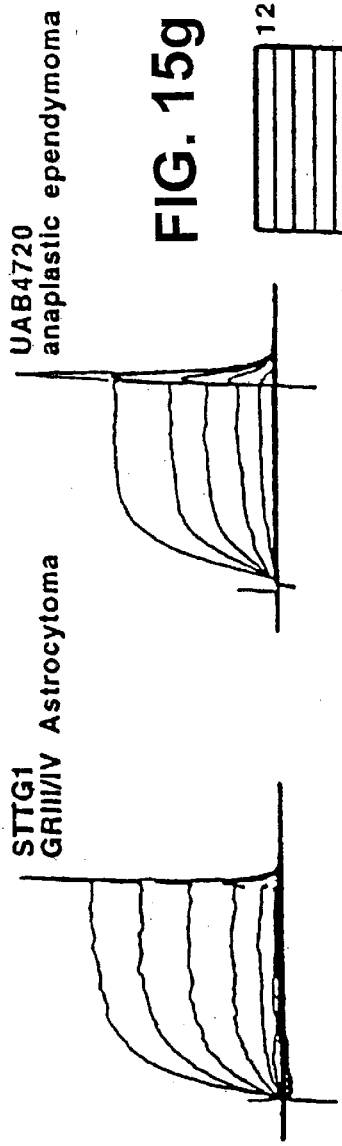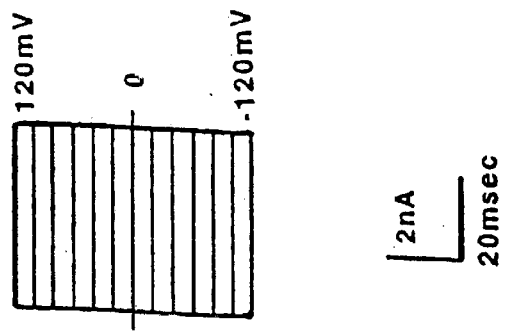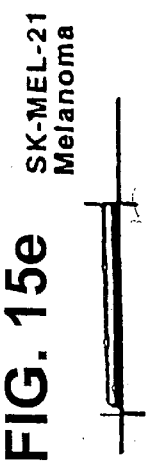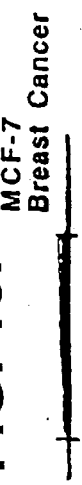

control

GST ctx-GST

Purification:     ClC5    Ctx
     Probe:           ClC5

METHOD OF DIAGNOSING AND TREATING GLIOMAS

This is a divisional which claims benefit of priority of provisional application U.S. Ser. No. 60/009,283 filed Dec. 27, 1995 of application Ser. No. 08/774,154 filed on Dec. 26, 1996 now U.S. Pat. No. 5,905,027.

BACKGROUND OF THE INVENTION

1. Field of the Invention

The present invention relates generally to the fields of cell physiology, neurology and neuro-oncology. More specifically, the present invention relates to a novel method of diagnosing and treating gliomas and meningiomas.

2. Description of the Related Art

Glial cells comprise a large proportion of the total cell population in the CNS. Unlike neurons, glial cells retain the ability to proliferate postnatally, and some glial cells still proliferate in the adult or aged brain. Uncontrolled glial proliferation can lead to aggressive primary intracranial tumors, the vast majority of which are astrocytomas, and therefore, of glial origin. Tumors of astrocytic origin vary widely in morphology and behavior, and, according to the 1993 WHO classification schema, can be separated into three subsets. Astrocytomas, the lowest grade tumors, are generally well-differentiated and tend to grow slowly. Anaplastic astrocytomas are characterized by increased cellularity, nuclear pleomorphism, and increased mitotic activity. They are intermediate grade tumors and show a tendency to progress to a more aggressive grade. Glioblastomas are considered the most aggressive, with poorly differentiated cells, vascular proliferation, and necrosis. Due to the common morphological heterogeneity of cells within a single tumor, such classification is not clear-cut and is somewhat unsatisfactory. The term "astrocyte-derived tumors" as used herein refers to astrocytomas. Meningiomas are tumor originating in the meninges.

Significant progress has been made in identifying physiologically important growth factors, receptors, and signal transduction pathways that control normal and malignant cell proliferation. It is now commonly accepted that growth factor binding leads to activation of oncogenes such as the ras/raf pathway, and ras in turn regulates gene expression through at least two mitogen-activated protein kinases. Interestingly, the ras/raf pathway is in crosstalk with the cAMP signaling cascade which is activated by numerous hormones and neurotransmitters.

Recent studies suggest that ion channels may function in regulating a cell's proliferative ability. For example, mitogen-stimulated lymphocytes show an upregulation in the expression of a high conductance potassium channel (15). In murine fibroblasts, activation of the ras/raf signaling cascade induces expression of a $Ca^{2+}$-activated $K^+$ channel that appears to be essential in the cells' proliferative response (17). The idea that ion channel expression may be necessary for cell cycle progression is also supported by observations that pharmacological blockade of ion channels can inhibit cell proliferation. This has been demonstrated in a number of cell types including melanoma (28), breast cancer cells (41), brown fat cells (30), and also in several glial cell types such as Schwann cells (5), retinal glial cells (32) and astrocytes (29).

Untransformed glial cells from which glial tumors may originate have been extensively characterized electrophysiologically (37). Surprisingly, they appear to be liberally endowed with voltage- and ligand-activated ion channels for $Na^+$, $K^+$, $Ca^{2+}$ and possibly $Cl^-$ ions. It is generally assumed that these ion channels perform homeostatic roles in the brain and may facilitate maintainance of $K^+$ and possibly $Na^+$ and $Cl^-$ ion concentrations in the extracellular space. In contrast to the numerous reports on ion channel expression and activity in nonneoplastic glial cells, electrophysiological properties of astrocytoma cells and the potential role of ion channels in growth control of astrocytomas remain largely unexplored. Inwardly rectifying $K^+$ currents have been demonstrated in several established astrocytoma cell lines (4).

Gliomas cells are a very heterogeneous cell population that lack common antigens. Consequently, the prior art is deficient in the lack of effective means of identifying and treating malignant gliomas. The present invention fulfills this longstanding need and desire in the art.

SUMMARY OF THE INVENTION

The present invention describes the expression of a chloride conductance with unique properties that selectively characterizes tumor-derived cells of glial origin. In the present invention, whole-cell patch-clamp techniques were used to characterize the biophysical and pharmacological properties of chloride channels in primary cultures and acutely isolated cells from biopsies of human astrocytomas and established cell lines. In all preparations, the expression of time-dependent and voltage-dependent outwardly rectifying currents was observed. These currents are sensitive to several $Cl^-$ channel blockers including chlorotoxin, a component of scorpion venom and also allow other anions to permeate. This chloride conductance is involved in the growth control of astrocytoma cells.

Expression of voltage activated ion channels was determined in primary cultures from 7 freshly resected human primary brain tumors and in a 7 established human astrocytoma cell lines. Astrocytoma cells consistently expressed voltage-dependent outwardly-rectifying currents. Currents activated at potentials greater than 45 mV and showed outward transients upon termination of voltage steps. Currents reversed at the $Cl^-$ equilibrium potential, suggesting that they were largely carried by $Cl^-$ ions. Altering $[K^+]_o$ or $[Na^+]_o$ did not alter currents; neither did replacement of $[K^+]_i$ by $Cs^+$ or $[Na^+]_i$ by NMDG. Anion substitution experiments suggest the following permeability sequence, determined from shifts in tail current reversal potential: $I^->NO_3^->Br^->Cl^->$acetate$>$isethionate$>F^->$glutamate. Currents were sensitive to the $Cl^-$ channel blockers chlorotoxin, DIDS, and DNDS, with chlorotoxin being most effective, yielding >80% block at 590 nM. DIDS (100 $\mu$M) and DNDS (100 $\mu$M) reduced currents by 33.5% and 38.2% respectively. Currents were also sensitive to zinc (100 $\mu$M, 47% block) and cadmium (25 mM, 42% block). Reducing $[Ca^{2+}]_o$ decreased outward currents by 58% and almost completely eliminated transients, suggesting that $Cl^-$ currents are $Ca^{2+}$-dependent. $Cl^-$ channel block resulted in altered cell proliferation as determined by $^3$H-thymidine incorporation, indicating that these channels are involved in astrocytoma growth control.

It is an object of the present invention to demonstrate that glial-derived tumor cells express a unique voltage-dependent $Cl^-$ channel which is not found in non-glial tumors, such as melanoma or breast carcinoma, nor in untransformed glial cells.

It is another object of the present invention to show that expression of this unique $Cl^-$ channel plays a role in the cells' abnormal proliferative state.

It is yet another object of the present invention to demonstrate the sensitivity of glioma $Cl^-$ channels to chlorotoxin.

It is still another object of the present invention to provide a monoclonal antibody which specifically binds to glial-derived or meningioma-derived tumor cells.

It is still another object of the present invention to demonstrate that glioma cells can be targeted and/or eliminated by a recombinant chlorotoxin fused to a cytotoxic protein.

It is still another object of the present invention to provide a method to screen for malignant gliomas.

It is still yet another object of the present invention to provide a method of treating malignant gliomas, including glioblastoma multiforme and astrocytomas.

Thus, in accordance with the aforementioned objects, in one embodiment of the present invention, there is provided an antibody which specifically recognizes an antigen in chloride channels of glial-derived tumor cells.

In another embodiment of the present invention, there is provided a pharmaceutical composition, comprising a ligand which binds specifically to glial-derived or meningioma-derived tumor cells and a pharmaceutically acceptable carrier.

In yet another embodiment of the present invention, there is provided a method of differentiating glial-derived or meningioma-derived neoplastic tumor tissue from non-neoplastic tissue, comprising the steps of: contacting a tissue of interest with an antibody that specifically recognizes an antigen in chloride channels of glial-derived tumor cells; and measuring the level of binding of the antibody, wherein a high level of binding is indicative that the tissue is neoplastic.

In still yet another embodiment of the present invention, there is provided a fusion protein, said protein comprised of: a ligand that specifically recognizes an antigen in chloride channels of glial-derived tumor fused to a cytotoxic moiety.

In still yet another embodiment of the present invention, there is provided a method of treating an individual having a glioma or meningioma, comprising the step of administering to said individual a pharmacologically effective dose of a composition of the present invention.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1(a–d) shows the whole-cell voltage-clamp recordings obtained from a representative human astrocytoma cell from cell line STTG1 and from a primary cultured astrocytoma cell (UAB4630). Cells were stepped to test potentials between −105 mV and 195 mV in 25 mV increments from a holding potential of 0 mV (inset). Cells showed large transients upon termination of voltage steps (star, A, C). Potential >45 mV resulted in fast-activating, non-inactivating outwardly rectifying currents (B, D).

FIGS. 2(a–b) shows that in order to determine the ion species that was carrying the outward current, the reversal potential of tail currents was analyzed. Cells were held at 0 mV, pulsed to 180 mV, and then pulsed in −20 mV steps from +120 mV to −120 mV (A, inset). Plotting tail current amplitudes (A, inset) as a function of voltage showed a reversal potential of 8 mV (B) in this cell.

FIGS. 3(a–e) shows the whole-cell leak subtracted current responses of STTG1 cells in response to a single 145 mV voltage step prior to and following substitution of extracellular Cl$^-$ with (125 mM) Br$^-$(A), I$^-$(B), NO$_3^-$(C), or F$^-$(D). Dashed lines represent control current with standard external solution and straight lines represent current with replacement solution. E) peak current-voltage relations obtained as in FIG. 1, with current normalized to that obtained with standard NaCl-rich external solution.

FIGS. 4(a–e) shows as in FIG. 3, whole-cell leak subtracted current responses of STTG1 cells prior to and following substitution of extracellular Cl$^-$ with (125 mM) acetate (A), glutamate (B), isethionate (C), or sucrose (D). As above, dashed lines represent control current with standard bath solution and straight lines represent current after replacement. E) peak current-voltage relations, normalized to current in presence of 125 mM Cl$^-$ as above.

FIGS. 5(a–i) shows the effect of bath application of chlorotoxin, DIDS (4,4'-Diisothiocyanostilbene-2,2'-disulfonic acid) and DNDS (4,4'-Dinitrostilbene-2,2'-disulfonic acid) on outward currents in STTG1 astrocytoma cells in response to test voltage pulses from −105 to +195 in 25 mV increments. Whole-cell currents are shown prior to (A) and following (B) bath application of 590 nM chlorotoxin. Chlorotoxin decreased outward currents by 81%. C) I-V relation of peak current amplitude as a function of applied voltage. Currents are also shown before and after application of 100 μM DIDS (D, E) and 100 μM DNDS (G, H). Current-voltage relations from those examples are shown in parts (F) and (I). The size of the outward current is reduced by DIDS at all potentials (33.5%±12.9 (n=5)). Similar to the effect of DIDS, DNDS caused a decrease in current amplitude at all potentials by 38.2%±13.3 (n=4).

FIG. 7 shows the comparison of the effects of channel blockers on outward currents. Effects are expressed as percent of normalized to current amplitude obtained in standard NaCl-rich external solution for pooling of experimental data. Error bars reflect SEM.

FIGS. 9(a–d) shows the whole-cell voltage-clamp recordings obtained from representative human astrocytoma cell (STTG1). Cells were stepped to test potentials between −120 mV and 120 mV in 20 mV increments from a holding potential of 0 mV. Cells showed large tail currents upon termination of voltage steps (arrow, A). Potential >0 mV resulted in fast-activating, non-inactivating outwardly rectifying currents (B). In order to determine the ion species that was carrying the outward current, the reversal potential of tail currents was analyzed. Cells were held at 0 mV, pulsed to 200 mV, and then pulsed in −20 mV increments from +120 mV to −120 mV (C). Plotting tail current amplitudes (C, inset) as a function of voltage showed a reversal potential of 0 mV (D).

FIG. 13 shows the biodistribution of Chlorotoxin binding sites as determined by injection of $^{125}$I-Ctx into a scid mouse bearing an experimental tumor.

FIGS. 14(a–c) shows the bath application of chlorotoxin (590 nM) inhibits outward currents in STTG1 cell line.

FIGS. 15(a–f) shows the representative whole-cell leak-subtracted currents from human tumor cell lines. Astrocytoma and glioblastoma cell lines were dominated by outwardly-rectifying voltage-activated chloride currents, whereas these currents were absent in cells from breast tumor and melanoma.

DETAILED DESCRIPTION OF THE INVENTION

Figure 6A:
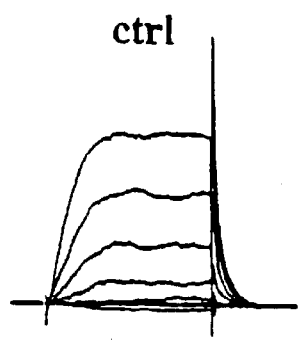
FIGS. 6(a–i) shows the effect of the zinc, cadmium, and calcium on outward currents. Bath application of 100 μM zinc led to a 47%±25.9 (n=3) decrease in peak currents (FIGS. 6, A–C), and 25 μM cadmium led to a 42%±18.5 (n=5) decrease (FIGS. 6, D–E). In bath solution with zero Ca$^{2+}$/5 mM EGTA, currents were decreased to 40% of that in control solution, containing 1 mM Ca$^{2+}$ (FIGS. 6, F–H).
Figure 6B:
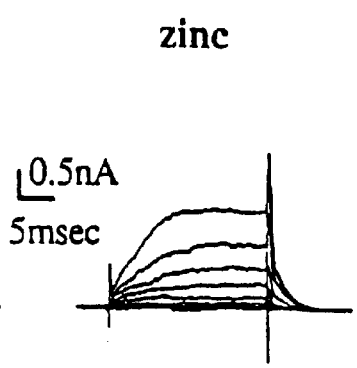
Figure 6C:
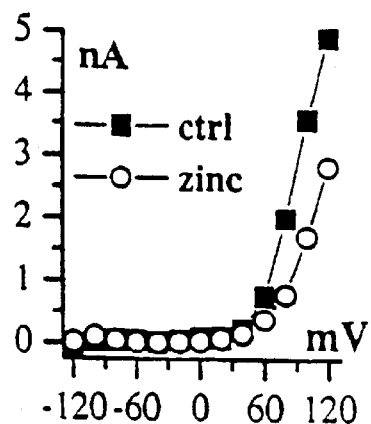
Figure 6D:
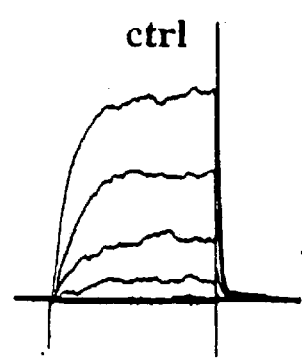
Figure 6E:
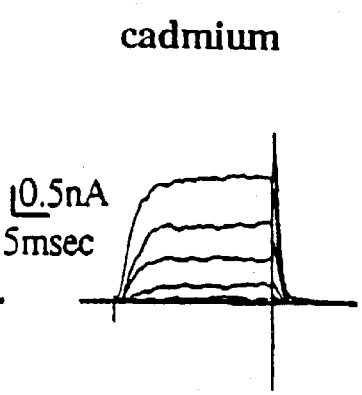
Figure 6H:
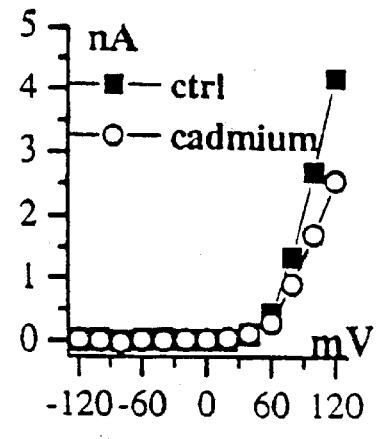
Figure 6F:
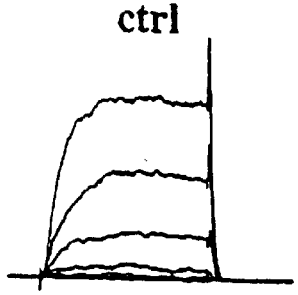
Figure 6G:
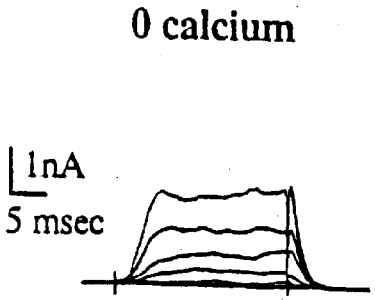
Figure 6I:
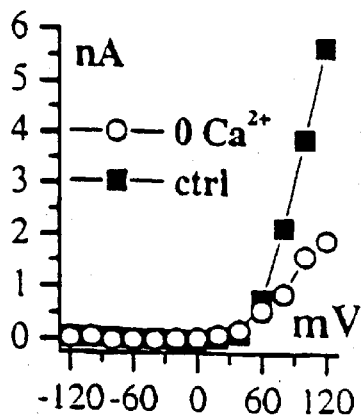
Figure 8:
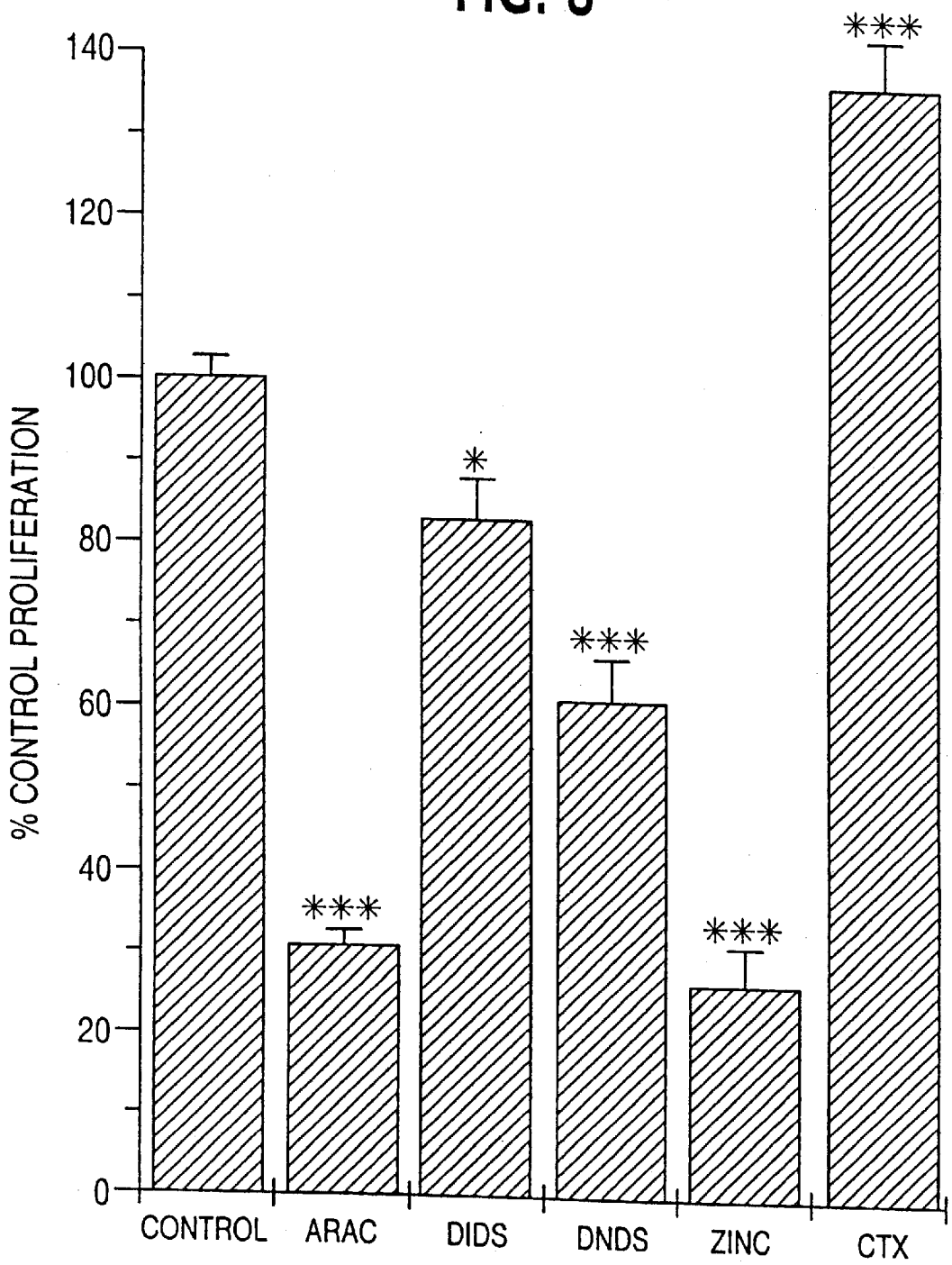
FIG. 8 shows the effects of the anti-mitotic agent Ara-C (10 μM), DIDS (200 μM), DNDS (200 μM), Zinc (200 μM), and chlorotoxin (600 nM) on astrocytoma proliferation, assessed as $^3$H-thymidine incorporation following 24 hour incubation with the agent of interest. Mean effects (expressed as cpm/μg protein, error bars=SD) were plotted for each agent tested in at least 6 experiments each (see text for details). As expected, incubation in the anti-mitotic agent Ara-C led to a 70% decrease in proliferation (SD=1.3309, N=17). The chloride channel blockers DIDS, DNDS, and zinc decreased proliferation by 16.4% (SD=20.0, N=16), 38.2% (SD=13.1, N=8), and 72.6% (SD=12.4, N=7), respectively. By contrast, incubation in chlorotoxin led to a 37.8% increase in proliferation compared to control (SD=5.7, N=8). Error bars reflect SEM.

Glioma cells, e.g. primary brain tumors derived from glial cells, express a unique membrane protein which constitutes a Cl⁻ ion channel termed herein Glioma Chloride Channel (GCC). In the brain, GCC is specific to gliomas and meningiomas and is not present in other cells. GCC was identified in 24/24 glioma patient biopsies, in 7/7 astrocytoma/glioblastoma cell lines and in 4/4 meningioma biopsies. GCC expression correlates with pathological tumor grade. GCC expression is preserved in intracranial xenograft tumors in scid mice, which provide an excellent animal model for the disease. GCC binds chlorotoxin, a 36 amino acid peptide, with high affinity and selectivity. Binding is preserved in both synthetic and recombinant form of chlorotoxin, and also if the molecule is altered in ways to carry fluorescent or cytotoxic moieties.

GCC is a specific marker and useful target for gliomas and meningiomas and can be used for diagnostic and therapeutic purposes. GCC can be targeted by antibodies to the protein and/or by molecules that bind to it. Specifically, chlorotoxin and chlorotoxin-like molecules (fusion proteins) can be used to specifically direct molecules bound on it to gliomas and meningiomas. These molecules include but are not limited to: $^{125}$I, $^{131}$I, fluorescent moieties, cytotoxic moieties including but not limited to ricin, saporin, pseudonomas exotoxin. Binding of chlorotoxin-like molecules or antibodies to GCC can be utilized to diagnose gliomas and meningiomas. Non-invasive strategies can be devised to utilize GCC expression for diagnostic purposes. For example, binding of $^{131}$I-Ctx to GCC can be visualized by PET scan.

Chlorotoxin inhibits GCC currents in a dose-dependent manner, with an apparent $IC_{50}$ of 950 nM. To assure that these effects were not caused by impurities in the venom, a recombinant toxin was also generated (in $E. coli$) after fusion to glutathione-S-transferase. The recombinant Ctx-GST fusion protein was even more effective in blocking GCC currents ($IC_{50}$∼540 nM), and an example of a whole-cell recording in the presence and absence of Ctx-GST and GST alone in a single cell is presented below. Chlorotoxin binds directly to GCC channels, as is the case in rat colonic epithelial cells (DeBin and Strichartz, 1991), where one single Ctx molecule is sufficient for channel block. However, it is possible that Ctx binds to a binding protein or receptor, and that subsequent changes in GCC currents are mediated indirectly, e.g. through G-proteins or second messengers.

The present invention is directed to novel methods of identifying, targeting and effectively suppressing the growth of glial-derived neoplastic cells. In one embodiment, the present invention provides a pharmaceutical composition, comprising an ligand which binds specifically to glial-derived or meningioma-derived tumor cells and a pharmaceutically acceptable carrier. In one embodiment, the ligand is an antibody which recognizes an antigen that is a glioma or meningioma specific chloride channel. Alternatively, the ligand is a chlorotoxin-like compound and is radiolabeled.

The present invention is also directed to a method of differentiating glial-derived or meningioma-derived neoplastic tumor tissue from non-neoplastic tissue, comprising the steps of: contacting a tissue of interest with an antibody that specifically recognizes an antigen in chloride channels of glial-derived tumor cells; and measuring the level of binding of the antibody, wherein a high level of binding is indicative that the tissue is neoplastic. Preferably, the level of antibody binding indicative of neoplastic tissue is from about 30% to about 90% of cells positively binding the antibody.

The present invention is also directed to a method of differentiating glial-derived or meningioma-derived neoplastic tumor tissue from non-neoplastic tissue, comprising the steps of: contacting a tissue of interest with labeled chlorotoxin which binds specifically to glial derived neoplastic tumor tissue; and measuring the binding of the labeled chlorotoxin, wherein a high level of binding is indicative that the tissue is neoplastic. Preferably, the chlorotoxin is selected from the group consisting of native, synthetic and recombinant chlorotoxin. Preferably, the labeled chlorotoxin is radiolabelded and the level of radiolabeled chlorotoxin binding affinity indicative of neoplastic tissue is from about 5 nM to about 5 micromolar. The radiolabeled chlorotoxin may be, e.g., $^{131}$I-chlorotoxin or $^{125}$I-chlorotoxin. Alternatively, the chlorotoxin is labeled with a fluorescent moiety and the fluorescently labeled chlorotoxin binding is determined by a method selected from the group consisting of fluoresecent microscopy and fluorescent activated cell sorting. The radiolabeled chlorotoxin binding may be determined, for example, using positron emission tomography scanning.

The present invention is also directed to a fusion protein, said protein comprised of: a ligand that specifically recognizes an antigen in chloride channels of glial-derived tumor fused to a cytotoxic moiety. In one embodiment, the ligand is a chlorotoxin-like protein. In another embodiment, the ligand is an antibody. Representative cytotoxic moieties include gelonin, ricin, saponin, pseudonomas exotoxin, pokeweed antiviral protein, diphtheria toxin, and complement proteins.

The present invention is also directed to a pharmaceutical composition, comprising the fusion protein of the present invention and a pharmaceutically acceptable carrier. The present invention is also directed to a method of treating an individual having a glioma or meningioma, comprising the step of administering to said individual a pharmacologically effective dose of any of the compositions of the present invention.

It is specifically contemplated that pharmaceutical compositions may be prepared using the novel antibodies and fusion protein of the present invention. In such a case, the pharmaceutical composition comprises the novel antibodies and fusion proteins of the present invention and a pharmaceutically acceptable carrier. A person having ordinary skill in this art would readily be able to determine, without undue experimentation, the appropriate dosages and routes of administration of the novel antibodies and fusion proteins of the present invention.

The following examples are given for the purpose of illustrating various embodiments of the invention and are not meant to limit the present invention in any fashion.

EXAMPLE 1
Primary Cultures of Human Astrocytomas (UAB Brain Tumor Research Laboratories, see Table 1 for details): Freshly resected brain tumor tissue was transported in ice-cold tissue culture medium and necrotic/hemorrhagic portions were removed aseptically. Discrete pieces of tumor tissue were minced finely, triturated, and plated in DMEM/F12 (Dulbecco's modified Eagle's medium mixed equally with Ham's Nutrient Mixture F12 supplemented with 10 mM HEPES, 2 mM L-glutamine) with 20% Fetal Bovine Serum (FBS, Atlanta Biologicals). Cells from minced fragments were replated onto uncoated 12 mm round coverslips for electrophysiology and for GFAP immmunocytochemistry. Acutely isolated tumor cells were prepared from fresh biopsy material, as described above with an additional trypsinization step in order to remove cellular debris, and were used for recordings 15–18 hours after plating.

EXAMPLE 2
Cell Lines

STTG1 cell line (American Type Culture Collection, Rockville, Md.) was grown in DMEM (Gibco) plus 10% FBS (Hyclone). Human Tumor Cell Lines: established cell lines, derived from human malignant gliomas (D54MG, U105MG, U251MG, and U373MG obtained from D. D. Bigner, Duke University) and extraglial human tumors (all from ATCC), were studied in long term (>100) passages (see TABLE I for details). Cells were maintained in DMEM/F12 supplemented with 7% heat-inactivated FBS (Atlanta Biologicals) at 37° C. in a 10% $CO_2$/90% air atmosphere. Cells attaining nearly confluent growth were harvested and replated onto uncoated 75 cm$^2$ flasks or uncoated 12 mm circular glass coverslips for electrophysiology and were used 36–72 hours after plating, unless otherwise noted. Viable cell counts were determined by trypan blue exclusion.

TABLE I

Primary cultures and established astrocytoma cell lines

| Cell Line Designation | Cell Type | Passage | GFAP | Cl- Current |
|---|---|---|---|---|
| Primary cultures | | | | |
| UAB4630 | GBM | 1 | unk | 8/8 |
| UAB8553 | GBM | 1 | + | 6/6 |
| UAB12983 | low-grade astrocytoma | 1 | + | 7/7 |
| UAB4613 | pilocytic astrocytoma | 1 | + | 6/6 |
| UAB4663 | pilocytic astrocytoma | 1 | + | 5/5 |
| UAB4720 | anaplastic ependymoma | 1 | + | 5/5 |
| UAB485923 | medulloblastoma | 0 | unk | 10/10 |
| Cell Lines | | | | |
| CH-235MG | GBM | >100 | + | 18/18 |
| D-54MG | GBM | >100 | + | 11/11 |
| SK-MG-1 | GBM | >100 | + | 10/10 |
| STGG1 | anaplastic astrocytoma | >100 | + | 470/470 |
| U-105MG | GBM | >100 | + | 10/10 |
| U-251MG | GBM | >100 | + | 28/28 |
| U-373MG | GBM | >100 | + | 10/10 |

Code:
GBM = glioblastoma multiforme;
+ = > 70% positive;
unk = unkown

EXAMPLE 3
Biopsy Tissue

Freshly resected human brain tumor tissue are collected during surgery in ice-cold tissue culture medium and necrotic/hemorrhagic portions are removed aseptically. Tissue is maintained for <15–20 min under 95/5% $O_2/CO_2$ until used for slicing. Ice-cold tissue are embedded in BactoAgar and cut into blocks of ~10×10 mm and glued to the bottom of a petri dish mounted to a Vibratome where 200 mm slices are cut. These are transferred to oxygenated saline and maintained at 37° C. until recording.

EXAMPLE 4
Xenografted Tumors in SCID Mice

C.B.-17 SCID mice are anesthetized by intraperitoneal administration of the following mixture: ketamine, 20 mg/ml plus xylazine, 0.3 mg/ml, in saline, at 0.07 ml/10 g of body weight. A midline scalp incision is made and a 0.5 mm burr hole is made at 1.5–2 mm to the right of the midline and at 0.5–1.0 mm posterior to the coronal suture. Tumor cells ($10^6$ D54 MG- human glioma cells in 5 ml final injection volume/ mouse) are suspended in excipient (serum free DMEM/F12+5% methyl cellulose). Intracranial injection is performed stereotactically using a 250 ml Hamilton syringe with a 30-gauge needle mounted on a Stoelting stereotaxic apparatus. The needle is inserted vertically through the hole to a depth of 2.5 mm. 45–60 seconds after injection, the needle is slowly withdrawn and the incision closed with 9 mm Michel wound clips. Mice are then returned to sterile microisolator polycarbonate cages placed over a heating pad until recovery, and provided autoclaved lab chow and sterile water a d libitum. Slices are obtained from anesthetized mice after decapitation. The brain is quickly removed and placed in ice-cold (4° C.) calcium-free ringers containing (in mM): NaCl 116; KCl 4.5; $MgCl_2$ 0.8; $NaHCO_3$ 26.2; glucose 11.1; N-2-hydroxyethlypiperazine-N'-2-ethanesulfonic acid (Hepes) 5. The solution is constantly bubbled with 95% $O_2$/5% $CO_2$ mixture. The brain is hemisected and mounted onto a vibratome slice-holder using cyanoacrylate glue. Transverse tissue slices (50–200 mM) are cut in cold oxygenated saline solution and subsequently transferred to a beaker filled with Ca containing saline at room temperature.

EXAMPLE 5
Electrophysiology

Current and voltage recordings were obtained using standard whole-cell patch-clamp techniques with an Axopatch-1D amplifier (Axon Instruments). Patch-pipettes were made from thin-walled borosilicate glass (WPI, TW150F-40) o.d. 1.5 mm, i.d. 1.2 mm and were filled with a solution containing (in mM): KCl 145, $MgCl_2$ 1, $CaCl_2$ 0.2, EGTA 10, Hepes 10, pH adjusted to 7.4 using Tris, unless otherwise noted. Pipettes were not fire-polished and typically had resistances between 2–5MΩ. Cells were continuously superperfused with saline solution, allowing for rapid (<30 seconds) exchange of bath volume. The standard bath solution contained, in mM: NaCl 122.6, KCl 5, $MgCl_2$ 1.2, $CaCl_2$ 1.0, $Na_2HPO_4$ 2.0, $NaH_2PO_4$ 0.4, $NaHCO_3$ 25.0, $Na_2SO_4$ 1.2, Glucose 10.5 (bubbled with 5% $CO_2$/95% $O_2$). The composition of bath solutions used for replacement studies is summarized in Table II. Drugs used to block ionic conductances were prepared freshly as stock solutions for each experiment and added to bath solution. Osmolality was measured with a vapor pressure osmometer (Wescor, Logan, UT) and adjusted to 308–312 mOsms.

For whole-cell recordings, cell capacitance compensation and series resistance compensation were used to minimize voltage errors. The amplifier reading of capacitance was used as the value for the whole-cell membrane capacitance. Series resistances, monitored at regular intervals throughout each experiment, were usually 5–10MΩ, and series resistance compensation was typically set to ~80%. Entrance potential, read from the amplifier at the time of entering the whole-cell configuration, was used to determine each cell's resting potential. Voltage-clamp recordings were used to search for voltage-activated currents and stimulation profiles were altered to fully activate chloride channels (pulses from −105 to 195 mV). Where indicated, P/4 leak subtraction was obtained using hyperpolarizing voltage steps to obtain leak currents. Current reversal potential (voltage at which I=0) was determined from IV plots in which tail current amplitudes were plotted as a function of voltage. Effects of channel blockers were assessed by comparing current traces, entrance potential, and reversal potential prior to and following drug application. Snap photographs were taken of each recorded cell using a CCD camera and a video printer for cataloging of cell size, location, and morphology. Recordings were made at room temperature, typically 20–25° C.

EXAMPLE 6
Proliferation Assay

Proliferation was studied quantitatively by determining incorporation of $^3$H-thymidine. In brief, cells were incubated for 24 hours in the continuous presence or absence of Ara-C (cytosine arabinoside, 10 μM), DIDS (200 μM), DNDS (200 μM), zinc (200 μM) or chlorotoxin (600 nM). Cells were incubated with 1 μCi/ml radiolabelled thymidine ([methyl-$^3$H]thymidine) for the final 4 hours (at 37° C.). Culture dishes were rinsed three times with ice-cold PBS and soublized with 0.3N NaOH for 30 minutes at 37° C. One aliquot (50 ml) was used for cell protein determination using the bicinchroninic assay (BCA; Pierce Rockford, Ill.). The remaining cell suspension was mixed with Ultima Gold, and radioactivity was determined with a scintillation counter. The results were expressed as cpm/μg protein.

EXAMPLE 7
Data Analysis

The theoretical equilibrium potentials were calculated according to the Nernst equation. The ion activities were adjusted from the ion concentrations used in solutions using activity coefficients obtained from Robinson and Stokes (34), which were 0.888, 0.886, and 0.888 for [$Na^+$], [$K^+$], and [$Cl^-$], respectively. Calculated equilibrium potentials under the imposed ionic gradients in control solution were $E_K$=−83.4 mV, $E_{Na}$=+62.6 mV, and $E_{Cl}$=+2.8 mV. For all experiments, mean values and standard deviation (SD) were

TABLE II

| | Composition of external solutions (in mM) | | | | | | | | | | | | | | | | |
|---|---|---|---|---|---|---|---|---|---|---|---|---|---|---|---|---|---|
| External Solution | $Na^+$ | $K^+$ | $HCO_3^-$ | Hepes | $Ca^{2+}$ | $Mg^{2+}$ | EGTA | $Cl^-$ | $Br^-$ | $F^-$ | $I^-$ | $NO_3^-$ | Isethionate | glutamate | acetate | sucrose | glucose |
| $HCO_3^-$ | 122 | 5 | 25 | — | 1 | 1.2 | | 132 | | | | | | | | | 10.5 |
| Hepes | 125 | 5 | | 32.5 | 1 | 1.2 | | 132 | | | | | | | | | 10.5 |
| NaBr | 125 | 5 | | 32.5 | 1 | 1.2 | | 132 | 125 | | | | | | | | 10.5 |
| NaF | 125 | 5 | | 32.5 | 1 | 1.2 | | 132 | | 125 | | | | | | | 10.5 |
| NaI | 125 | 5 | | 32.5 | 1 | 1.2 | | 132 | | | 125 | | | | | | 10.5 |
| $NaNO_3$ | 125 | 5 | | 32.5 | 1 | 1.2 | | 132 | | | | 125 | | | | | 10.5 |
| Isethionate | 125 | 5 | | 32.5 | 1 | 1.2 | | 132 | | | | | 125 | | | | 10.5 |
| Glutamate | 125 | 5 | | 32.5 | 1 | 1.2 | | 132 | | | | | | 125 | | | 10.5 |
| NaAcetate | 125 | 5 | | 32.5 | 1 | 1.2 | | 132 | | | | | | | 125 | | 10.5 |
| 0 NaCl | 0 | 5 | | 32.5 | 1 | 2.2 | 5 | 7.4 | | | | | | | | 250 | 10.5 | computed from raw values entered into a spreadsheet (Excel, Microsoft). These data were exported to a scientific graphing and data analysis program (ORIGIN, MicroCal). Data were graphed as mean±S.E.M. Statistics were computed from raw data. For physiological effects of channel blockers, a paired, one-tailed t-test was used. For proliferative effects of channel blockers, results were analyzed using ANOVA test for multiple comparisons. DIDS (4,4'-Diisothiocyanostilbene-2,2'-disulfonic acid), DNDS (4,4'-Dinitrostilbene-2,2'-disulfonic acid), Ara-C, and all other drugs were all purchased from Sigma. Chlorotoxin was purchased from Lanoxin (Accurate Chemical and Scientific Corp., Westbury, N.Y.).

EXAMPLE 8
Results

Whole-cell voltage clamp recordings were obtained from primary cultures of 7 freshly resected primary human brain tumors. In addition, a human anaplastic astrocytoma cell line, STTG1, was studied. The majority of STTG1 and primary-cultured cells were positive for glial fibrillary acidic protein (GFAP). Cells chosen for recordings were typically alone or isolated from other cell clusters and displayed bipolar, fibroblast-like morphology. Under normal recording conditions, time- and voltage-dependent outward currents were observed in all (N=490) recorded STTG1 astrocytoma cells and in all recorded primary cultured astrocytoma cells (N=60). Recordings from acutely isolated tumor cells were also obtained within 15–18 hours of plating (UAB485923, N=10). Currents were qualitatively similar in all preparations. The resting potential, determined as the entrance potential with KCl-containing pipette solution, was −14.1 mV (N=490, SD=14.6, SEM=0.66) and −20.15 mV (N=60, SD=17.54, SEM=2.28), in cell lines and primary cultures, respectively.

EXAMPLE 9
Chloride Currents in Human Astrocytoma Cells

Representative examples of whole-cell recordings from an STTG1 human astrocytoma cell and an astrocytoma cell from primary culture (UAB4630) in response to depolarizing voltage steps are displayed in FIG. 1. The cells were stepped from a holding potential of 0 mV to a series of test potentials between −105 mV and 195 mV in 25 mV increments. Potential >45 mV resulted in fast activating, non-inactivating outward currents. Cells showed large outward transients upon termination of voltage steps (FIGS. 1A and C). The IV relation plotting peak current amplitude as a function of voltage (FIGS. 1B and D) showed pronounced voltage dependence and outward rectification for both the transients (FIGS. 1 B, D "*") and steady-state currents (FIGS. 1B, 1D "x"). Mean conductance of 36 primary cultured cells was 5.67 nS (SD=4.62, SEM=0.77) and of 50 STTG1 cells was 5.29 nS (SD=3.63, SEM=0.51) (determined at 145 mV). To account for differences in cell size, values were normalized to membrane capacitance, yielding specific conductances of 195 pS/pF and 208 pS/pF, respectively. To determine the ion species that was carrying the outward current, the reversal potential of tail currents were analyzed. Therefore, cells were held at 0 mV, pulsed to 180 mV, and then stepped in −20 mV increments from +120 mV to −20 mV (FIG. 2A). Plotting tail currents as a function of voltage showed a reversal potential of 8 mV (FIG. 2B) in this example. Analysis of 12 primary cultured cells yielded a mean reversal potential of 0.1 mV (SD=11.3) and of −4.6mV (N=48, SD=14.1) in STTG1 cells. Under the imposed ionic gradients ($E_{Cl^-}=+2.8$, $E_{K^+}=-83.4$, $E_{Na^+}=+62.6$ mV), this is compatible with a reversal potential expected for either a Cl⁻-selective current or a nonselective cation current. Cells from all studied primary cultures and all STTG1 cells displayed such outwardly rectifying currents, and subsequent analysis did not distinguish between these two preparations.

EXAMPLE 10

Channel Selectivity for Cl⁻

In order to determine the ion selectivity of the outward current, all but 7 mmol/L of the Cl⁻ in the bath solution was substituted with the sodium salts of a number of other monovalent anions (See Table II for composition of solutions), while keeping the pipette [Cl⁻] constant (147.4 mM). To facilitate ion replacement studies, Hepes-buffered solutions were used; changing to Hepes-buffered solution as compared to $HCO_3^-$-buffered solution by itself did not alter currents, suggesting that $HCO_3^-$ does not permeate the channel under these conditions. Recordings obtained in Hepes- and $HCO_3^-$-buffered external solutions were virtually indistinguishable, with no change in current amplitude or tail current reversal potential (data not shown).

FIG. 3 shows examples of whole-cell leak-subtracted current responses of human astrocytoma cells to test pulses stepped from a holding potential of 0 mV to 145 mV prior to and following substitution of bath chloride with the halide anions bromide (A), iodide (B), nitrate (C), and fluoride (D). Bromide, iodide, and nitrate increased outward currents, whereas fluoride substitution led to decreased currents. For each experiment, complete IV curves were plotted in (E). To compare I-V relations, currents were normalized to control currents with Cl⁻ as the external anion as the membrane was stepped from 0 mV to a series of potentials between −105 and +195 mV. Largest currents in Cl⁻-containing control solution were arbitrarily defined as 1. Currents in iodide and nitrate exceeded Cl⁻ currents by >2-fold. Similarly, FIG. 4 shows the whole-cell leak-subtracted current responses with the same experimental protocol as in FIG. 3 prior to and after substitution with (A) acetate, (B) glutamate, (C) isethionate, and (D) sucrose. Acetate and isethionate led to decreased outward currents, while glutamate and sucrose virtually eliminated outward currents. The current voltage relations for the non-halide substitutions normalized to normal NaCl-rich bath solution are shown in part (E). The selectivity for the different anions was calculated from the shift of the reversal potential under the imposed ionic gradients according to the Goldman-Hodgkin-Katz equation:

$$\Delta E_{rev} = E_{rev, anion} - E_{rev, Cl^-} = (RT/zF)\ln(P_{anion}[\text{anion}]_o/P_{Cl}[Cl]_o,$$

where R, T, and F have their usual meanings. In this calculation, it was assumed that the currents measured under the conditions of the experiment were carried solely through Cl⁻ channels. In total, the permeability of seven different anions was tested. Table III summarizes the changes in the values of $E_{rev}$ for equimolar replacement of chloride by test anions and the calculated permeability ratios ($P_{anion}/P_{Cl}$) These data suggest the following relative permeability sequence:

I⁻>NO₃⁻>Br⁻>Cl⁻>acetate>isethionate>F⁻>glutamate.

TABLE III

| | | Anion selectivity. | | |
|---|---|---|---|---|
| Na⁺-Anion | MW | $\Delta E_{rev}$(mV) | $P_{anion}/P_{Cl}$ | N |
| Chloride | 58.45 | — | — | 48 |
| Acetate | 82.04 | 4.0 ± 0 | 0.90 ± 0.02 | 3 |
| Bromide | 102.9 | −15.5 ± 6.3 | 1.95 ± 0.47 | 3 |
| Fluoride | 42.0 | 24.6 ± 3.0 | 0.41 ± 0.05 | 3 |
| Glutamate | 169.1 | 29.8 ± 2.3 | 0.33 ± 0.18 | 2 |
| Iodide | 149.9 | −20.8 ± 7.5 | 2.44 ± 0.65 | 5 |
| Isethionate | 148.1 | 18.5 ± 0.7 | 0.51 ± 0.01 | 3 |
| Nitrate | 85.01 | −15.8 ± 8.8 | 2.02 ± 0.58 | 4 |
| (Sucrose) | 342.3 | 32.2 ± 17.8 | — | 3 |

Table 3: Anion selectivity—The reversal potential ($E_{rev}$) was determined in each test solution by plotting peak tail current amplitude against the applied voltage step after cells were stepped to 180 mV and then brought from +120 mV to −120 mV in −20 mV increments. Results are expressed as the mean change in $E_{rev}$ from control solution containing NaCl. The permeability ratio $P_{anion}/P_{Cl}$ was determined using the Goldman-Hodgkin-Katz equation.

EXAMPLE 11
Effect of Cl⁻ Channel Blockers

The outward current pharmacologically were further characterized by examining the effect of several established Cl⁻ channel blockers, including chlorotoxin, DIDS, and DNDS. FIG. 5 shows representative whole-cell leak subtracted traces and current-voltage relations before and after bath addition of chlorotoxin, DIDS (4,4'-Diisothiocyanostilbene-2,2'-disulfonic acid) and DNDS (4,4'-Dinitrostilbene-2,2'-disulfonic acid). Bath application of 590 nM chlorotoxin reduced both the steady state and transient amplitude evoked by voltage steps from −105 to +195mV by 81.9%±0.88 (n=4) of the control value (FIGS. 5A–C). This effect was partially reversible. Chlorotoxin was also effective at higher concentrations in blocking Cl⁻ currents when applied to the cytoplasmic face (60.44% at [chlorotoxin]$_i$=2.5 μM, N=7, SD=17.8, data not shown). Chlorotoxin is a protein having 36 amino acids that is derived from scorpion venom toxin that was originally described as a blocker of small conductance Cl⁻ channels in epithelial cells (8). In order to ensure that the effects of chlorotoxin did not result from any contaminants in the venom toxin, the peptide was synthesized and comparable inhibition of currents with the synthetic toxin were observed (data not shown). As above, currents are shown before and after application of 100 μM DIDS (FIGS. 5D, 5E) and 100 μM DNDS (FIGS. 5G, 5H). Current-voltage relations from those examples are shown in parts (F) and (5I). The size of the outward current was reduced by DIDS at all potentials (33.5%±12.9(n=5)). Similar to DIDS, DNDS caused a decrease in current amplitude at all potentials by 38.2%±13.3 (n=4). DIDS and DNDS were more effective in blocking currents when applied to the cytosolic face, albeit at higher concentrations (200 μM, 50%±10.9 (N=3) and 62% (N=1), respectively, data not shown). The action of both drugs was partly reversible with short exposure times, though the recovery was never complete.

The effects of the heavy metals zinc and cadmium on outward currents were also examined. These drugs have been shown to block Cl⁻ currents in T lymphocytes (35) and Schwann cells (33).

Bath application of 100 μM zinc led to a 47%±25.9 (n=3) decrease in peak currents (FIGS. 6, A–C), and 25 μM cadmium led to a 42%±18.5 (n=5) decrease (FIGS. 6, D–E). Since $Cd^{2+}$ is also a blocker of voltage-dependent $Ca^{2+}$ channels, it is possible that reduced currents may have resulted indirectly from reducing $Ca^{2+}$ influx. To help elucidate whether this may have been the case, a bath solution was applied in which all $Ca^{2+}$ had been removed, with the addition of 5 mM EGTA. In a zero calcium environment, currents were decreased to 42.6%±16.8 (n=5) of that in control solution, containing 1 mM $Ca^{2+}$ (FIGS. 6, F–H), suggesting that, indeed, Cl⁻ currents are at least partially dependent on $[Ca^{2+}]_o$. A summary of the pharmacological effects on current amplitude is shown in FIG. 7, with the values expressed as percent of control current in standard external solution. Based on the ion replacement studies and pharmacology, it was concluded that the outwardly rectifying currents were mediated by anions. Under physiological conditions, the current would be carried by Cl⁻, thus it can be referred to as a Cl⁻ current.

EXAMPLE 12
Cl⁻ Channels and Astrocytoma Proliferation

Given that these Cl⁻ currents were consistently present in all astrocytoma cells tested from both primary cultures of surgical specimens and from established human astrocytoma cell lines, whether Cl⁻ currents influence astrocytoma proliferation was examined. Although the effects of Cl⁻ channel blockade on cell proliferation have been reported in Schwann cells (40) and in B lymphocytes (7), the importance of Cl⁻ ion channels in glia cells has never been shown. Cells were cultured in the continuous presence of the anti-mitotic agent Ara-C (10 μM), DIDS (200 μM), DNDS (200 μM), Zinc (200 μM), or chlorotoxin (600 nM) and compared the rate of proliferation to untreated (control) sister cultures. Cells were treated at 2 days in culture (DIC) and proliferation was assayed 24 hours later, at 3 DIC, a period of high proliferation of untreated control cultures. As expected, incubation in the anti-mitotic agent Ara-C led to a 70% decrease in proliferation (SD=1.3309, N=17). The putative chloride channel blockers DIDS, DNDS, and zinc decreased proliferation by 16.4%(SD=20.0, N=16), 38.2% (SD=13.1, N=8), and 72.6% (SD=12.4, N=7), respectively. By contrast, incubation in either the native or synthetic venom toxin chlorotoxin led to an increase in proliferation compared to control (mean=37.8%, SD=5.7, N=8 and mean=28.4%, SD=16.34, N=9) respectively).

The present invention identified a voltage-dependent, outwardly-rectifying Cl⁻ current in human astrocytoma cells. This current was present in all cells studied in both primary cultures of human astrocytomas and in an established human astrocytoma cell line. Cells showed large outward transients upon termination of voltage steps and reversed close to the calculated equilibrium potential for chloride. Upon replacement with various anions, the current reversal potential shifted in accordance with an anion-selective channel towards the new $E_{Cl}$. Currents were sensitive to application of chloride channel blockers chlorotoxin, DIDS, DNDS, cadmium, and zinc. Under physiological conditions, the current would be carried by Cl⁻, so that currents were considered chloride currents. The presence of the current was surprising in light of the fact that non-neoplastic glial cells are typically characterized by high levels of expression of voltage-gated K⁺ channels; no appreciable contribution from K⁺ currents to whole-cell outward currents was observed in all cells tested.

Outwardly rectifying chloride currents have been described in many epithelial tissues including respiratory cells (24), submandibular gland (19), lacrimal gland (9), pancreatic duct cells (18), epididymis (31), and sweat gland (23), and in non-epithelial cells such as lymphocytes (11), squid axon (18), and rat skeletal muscle (3). The physiological function of these outwardly rectifying channel in cell types other than secretory epithelia remains unclear. In the latter, they are believed to participate in transepithelial solute transport and volume regulation (10).

The current observed in astrocytoma cells, although similar to epithelial cells in its sensitivity to $Cl^-$ channel blockers, shows several differences: First of all, in some preparations, such as fetal pancreas (13), fetal epididymis (31), and pancreatic ductal cells (2), chloride currents show little or no voltage dependence. Secondly, another class of chloride channels shows a peculiar voltage-dependence with activation near 0 mV and inactivation with potentials more than 20 mV in either direction (3,27,36). Astrocytoma $Cl^-$ channels are strongly voltage-dependent at all potentials >50 mV. In this regard, they are most similar to $Cl^-$ channels found in human macrophages(16), necturus enterocytes(12), squid axon(18) and sheep parotid gland (19). Thirdly, in some cell types, such as colon muscle (1), submandibular gland (19), rat muscle (3), and A6 epithelia cells (27), chloride channels do not show spontaneous activity in whole cell recordings and channel activation occurs only in excised patches. In contrast, astrocytoma $Cl^-$ currents could be easily recorded in every recording in the whole-cell configuration.

The permeability sequence of the chloride channel in astrocytoma cells does not correlate with the hydrated ion radii ($NO_3^- > Cl^- > I^- > Br^-$) or the mobility of ions in aqueous solution ($Br^- > I^- > Cl^- > NO_3^-$). The sequence most closely resembles the lyotrophic series ($I^- > NO_3^- > Br^- > Cl^- > F^-$), which reflects the ability to denature macromolecules or to bind or absorb to proteins or lipid-water interfaces (6). The anion selectivity sequence here differs in only minor detail from those reported for outwardly rectifying channels in other tissues: submandibular duct gland ($SCN^- > NO_3^- > I^- > Cl^- > Br^- >$ acetate)(19), canine airway epithelia ($SCN^- > NO_3^- > I^-$ $Br^- > NO_3^- > Cl^-$) (25), rat lacrimal gland ($I^- > NO_3^- > Br^- > Cl^- > F^- >$ isethionate>glutamate) (9) and necturus enterocytes ($SCN^- > I^- > Br^- > Cl^- > F^- >$ gluconate) (12). Typically, replacement of $Cl^-$ by large organic anions results in the virtual abolishment of $Cl^-$ currents. Similarly, in the recordings herein, currents were almost eliminated after glutamate or sucrose replacement.

Brismar and Collins (1989) tested various human astrocytoma cell lines and found a high density of inwardly rectifying potassium channels active at or near resting potential. The current component active at potentials more negative than 0 mV was blocked by $Cs^+$ and was dependent on $[K^+]_o$, such that replacement with high $K^+$ solutions led to an increase in the inward currents. Upon closer examination, the current component active at potentials more positive than 0 mV was insensitive to ion replacements of $Na^+$ or $K^+$ and was also insensitive to $Cs^+$ blockade. This is the range of voltage steps that produces an IV relation most similar to the one observed here.

These authors did not further investigate the current contributions >0 mV. No appreciable contribution of $K_{ir}$ currents was seen herein. It is possible that the cells' proliferative state or differences in culture conditions may alter the presence of $K_{ir}$. However, unlike Brismar and Collins, the present invention also examined cells prepared from primary cultures of surgical specimens from astrocytomas and did not see any appreciable $K_{ir}$ currents.

Recently, a chloride current has been described in an astrocytoma cell line (U373MG) that is only activated by hyposmotic conditions but not present under normosmic conditions. These authors report that outward currents are sensitive to one of the chloride channel blockers used herein, namely DIDS, in addition to some additional putative channel blockers. Though the IV relations appear similar to those described in the same voltage range, currents do not show the large outward transients upon termination of the voltage steps characteristic. Most importantly, the currents in these cells were not active under normosmic conditions, and the cells must have been exposed to hyposmotic bath solutions before the chloride currents could be evoked. Again, these authors did not investigate cells from surgical specimens in their studies. In addition, the presence of an anion current in cultured rat cortical astrocytes has been recorded which is active only in 1–2 out of 100 excised patches in normosmic conditions and with increased frequency in hyposmic conditions (20). Whole cell $Cl^-$ currents were previously recorded in cultured rat astrocytes; however, these currents differ markedly in their voltage dependency and relative permeability to anions from that described here for several reasons (14). The present invention discloses the presence of outwardly-rectifying, voltage-dependent chloride currents in biopsies prepared from surgical specimens from 6 different human astrocytomas and from 7 different established human astrocytoma cell lines (39) under normosmic conditions.

Furthermore, the present invention recorded $Cl^-$ currents in the cell line U373MG in addition to other established astrocytoma cell lines (CH-235MG, D-54MG, SK-MG-1, U-105MG, U251MG. Moreover, the currents were observed in all cells under normal conditions, with osmolality of each solution measured and matched to the osmolality of the growth medium.

The precise role of this chloride conductance in astrocytoma cells is unclear. Ion channels have been shown to be part of the proliferative response in a number of cell types and in cultures of normal glial cells, the activity of $K^+$ channels is required for cell proliferation, since $K^+$ channel blockade leads to decreased proliferation. Potassium channels have been implicated in the proliferative response in a number of other cell types, including human melanoma cell lines (28), cultured brown fat cells (30), and Schwann cells, the principle glial cells in the peripheral nervous system (5). The present invention demonstrates that the link between channel activity and proliferation is more widespread. Modulation of channels may result from both long-term changes in gene expression and short-term modulation of pre-existing channel proteins.

A link between chloride channels and the proliferative response has only recently been suggested. In cultured B cells, the stilbene disulphonates and putative chloride channel blockers SITS and DIDS were found to be effective mitogens and directly stimulated proliferation (7). Moreover, the mitogenic responses to DIDS were routinely larger than those obtained with the B cell mitogen LPS. These experiments imply that there is a signal transduction pathway leading to cell proliferation that directly involves anion movement across the cell membrane. In Schwann cells, SITS and DIDS application leads to a 2- to 5-fold enhancement of proliferation in both unstimulated and mitogen stimulated proliferation (40). The present invention observed a decrease in proliferation by DIDS, DNDS, and zinc and a 37% enhancement of astrocytoma proliferation following application of chlorotoxin. One possible explanation is that the stilbene derivatives are affecting ion transport mechanisms, whereas chlorotoxin is a more specific ion channel inhibitor. Thus, the present invention shows that Cl⁻ channels participates in the proliferative response in these cells.

EXAMPLE 13
Electrophysiology

For the following studies, the electrophysiology format was as follows: standard current and voltage recordings were obtained using the whole-cell patch-clamp technique with an Axopatch-1D amplifier (Axon Instruments). Cells were continuously superperfused with bicarbonate-buffered saline at room temperature containing, in mM: NaCl 122.6, KCl 5, $MgCl_2$ 1.2, $CaCl_2$ 1.0, $Na_2HPO_4$ 2.0, $NaH_2PO_4$ 0.4, $NaHCO_3$ 25.0, $Na_2SO_4$ 1.2, Glucose 10.5 (bubbled with 5% $CO_2$). Electrodes (WPI, TW150F-40) o.d. 1.5 mm, i.d. 1.2 mm were filled with (in mM): KCl 145, $MgCl_2$ 1, $CaCl_2$ 0.2, EGTA 10, Hepes 10, pH adjusted to 7.4 using Tris, unless otherwise noted. Entrance potential, read from the amplifier at the time of entering the whole-cell configuration, was used to determine each cell's resting potential. Voltage-clamp recordings were used to search for voltage-activated currents and stimulation profiles were altered to fully activate chloride channels (pulses from −120 to 120 mV). Current reversal potential (voltage at which I=0) was determined from IV plots in which tail current amplitudes were plotted as a function of voltage. Effects of channel blockers were assessed by comparing current traces, entrance potential, and reversal potential prior to and following drug application. Recordings were made at room temperature.

EXAMPLE 14
Ion Channel Expression in Human Astrocytoma Cells

Whole-cell voltage clamp experiments were performed on primary cultures and on established cell lines—both derived from human astrocytomas (see TABLE IV). All of the primary cultures and all of the cell lines studied (with the exception of one primary culture not tested) were >80% GFAP-positive. FIG. 9 shows typical whole-cell recordings from an anaplastic astrocytoma cell (STTG1). Depolarizing voltage steps activated time- and voltage-dependent outward currents in all (N=577) recorded astrocytoma-derived cells. The resting potential, determined as the entrance potential with KCl-containing pipette solution, was −14 mV(SD=15, SEM=0.62, N=577). Cells were stepped to test potentials between −120 mV and 120 mV in 20 mV increments from a holding potential of 0 mV. Cells showed large tail currents upon termination of voltage steps (FIG. 9A). Potential >0 mV results in fast activating, non-inactivating outward currents. The IV relation plotting peak current amplitude as a function of voltage (FIG. 9B) showed pronounced outward rectification. In order to determine the ion species that was carrying the outward current, the reversal potential of tail currents was analyzed. Therefore, cells were held at 0 mV, pulsed to 200 mV, and then pulsed in −20 mV increments from +120 mV to −120 mV (FIG. 9C). Plotting tail currents as a function of voltage showed a reversal potential of 0 mV. Under the imposed ionic gradients ($E_{Cl^-}$=2.8, $EK^+$=−83.4, $ENa^+$=67.3), this is compatible with that expected for either a Cl⁻-selective current or a nonselective cation current (FIG. 9D).

TABLE IV

Primary cultures and established astrocytoma cell lines

| Cell Line Designation | Cell Type | Passage | GFAP | Cl⁻- Current |
|---|---|---|---|---|
| Astrocytomas | | | | |
| UAB4630 | GBM | 1 | unk | 8/8 |
| UAB8553 | GBM | 1 | + | 6/6 |
| UAB12983 | LGA | 1 | + | 7/7 |
| UAB4613 | PA | 1 | + | 6/6 |
| UAB4663 | PA | 1 | + | 5/5 |
| UAB4720 | AE | 1 | + | 5/5 |
| CH-235MG | GBM | >100 | + | 18/18 |
| D-54MG | GBM | >100 | + | 11/11 |
| SK-MG-1 | GBM | >100 | + | 10/10 |
| STGG1 | AA | >100 | + | 470/470 |
| U-105MG | GBM | >100 | + | 10/10 |
| U-251MG | GBM | >100 | + | 28/28 |
| U-373MG | GBM | >100 | + | 10/10 |
| Non-glial tumors | | | | |
| SK-MEL-3 | mela. | 5 | − | 0/10 |
| MCF-10A | N.B. | 41 | − | 0/5 |
| MCF-7 | B.CA | 155 | − | 0/12 |
| TE671 | R. | 17 | − | 0/12 |
| IMR-32 | R. | 57 | − | 0/6 |
| SK-N-SH | R. | 53 | − | 0/5 |

Code:
GBM = glioblastoma multiforme;
LGA: low grade astrocytoma;
PA" pilocytic astrocytoma;
AE: anaplastic ependymoma;
AA: anaplastic astrocytoma;
mela.: melanoma;
N.B.: normal breast;
B.CA: breast cancer;
R. rhabdomyosarcoma;
+ = > 80% positive;
unk = unkown

EXAMPLE 15
Cancer Relevance

Glioma cells express a unique transmembrane Cl⁻ ion channel that binds a venom toxin (chlorotoxin) with very high affinity. The high affinity for chlorotoxin allow the development of glioma-specific agents including marker compounds for rapid diagnosis and immunotoxins for therapeutic treatment. Since this protein is only shared among malignant glioma cells and meningioma cells it could be targeted by reagents that bind to the toxin binding site, or, following isolation of the protein, antibodies could be used to selectively eliminate cells expressing this protein. This approach has a high likelihood to yield new strategies for more specific and more effective therapeutic modalities for this uniformly fatal disease.

EXAMPLE 16
Expression of GCC in Acute Patient Biopsies

Figure 10B:
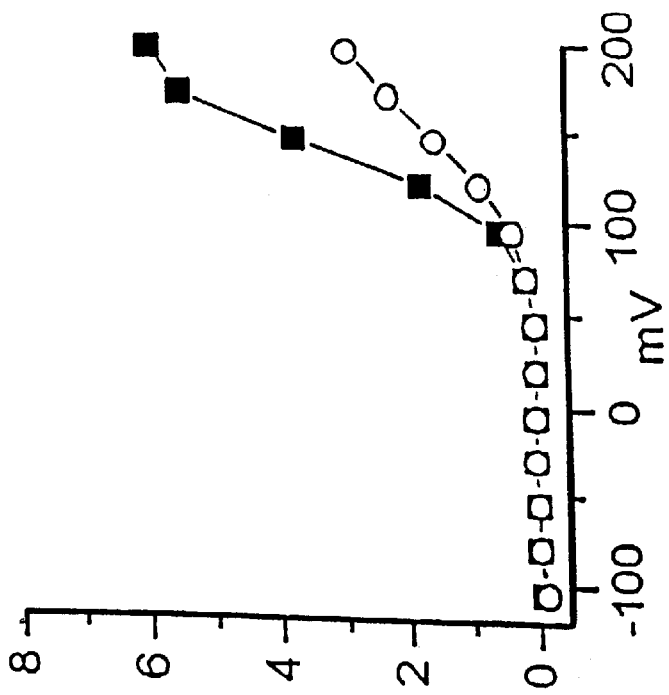
FIGS. 10(a–b) shows the recordings from a glioma cell in biopsy tissue from a GBM in response to 13 depolarizing voltage steps ranging from −105 to 195 mV.
Figure 10A:
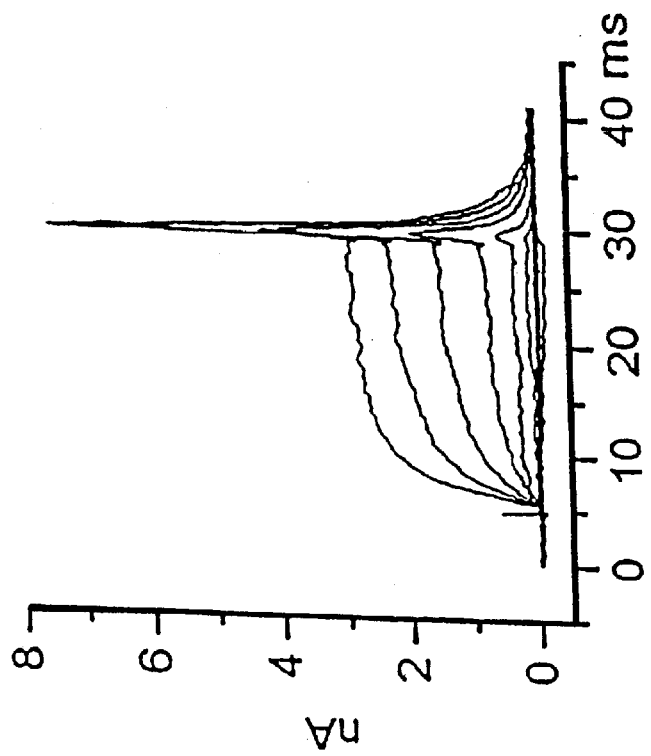

Biopsies from 24 patients diagnosed with gliomas were thoroughly investigated histopathologically. Electrophysiological recordings and immunohistochemical methods were used to detect GCC. Expression was observed in all patients and spanning in age from 0.5 to 77 years and independent of pathological grade of the tumor. An example of a representative recording is shown in FIG. 10. Evidence for the expression of GCC was obtained in 4/4 biopsies of patients diagnosed with meningioma. A list of patient cases studied in which GCC was identified is presented in TABLE V.

TABLE V

| Case # | age | sex | tissue pathology | location | WHO grade | Slice/Culture | # cells | Passage |
|---|---|---|---|---|---|---|---|---|
| 1 | 5 | F | pilocytic astrocytoma | hypothalamus | I | S/C | 9/25 | 0 |
| 2 | 7 | F | pilocytic astrocytoma | cerebellum | I | S/C | 10/12 | 0 |
| 3 | 11 | M | pilocytic astrocytoma | posterior fossa | I | C | 10 | 0 |
| 4 | 3 | M | pilocytic astrocytoma | cerebellum | I | C | 3 | 0 |
| 5 | 14 | F | pilocytic astrocytoma | thalamus | I | C | 6 | 1 |
| 6 | 8 | F | pilocytic astrocytoma | temporal lobe | I | C | 5 | 1 |
| 7 | 4 | M | pilocytic astrocytoma | temporal lobe | I | S/C | 7/10 | 0 |
| 8 | 1 | M | pilocytic astrocytoma | posterior fossa | I | S | 6/— | — |
| 9 | 0.5 | M | pilocytic astrocytoma | posterior fossa | I | S/C | 7/6 | 0 |
| 10 | 0.5 | F | papilloma | ventricular | I/II | C | 6 | 0 |
| 11 | 13 | F | subependymalgiant cell astrocytoma | frontal lobe | I/II | S/C | 12/8 | 0 |
| 12 | 56 | F | low grade astrocytoma | parietal lobe | II | C | 5 | 1 |
| 13 | 10 | M | anaplastic ependymoma | occipital lobe | III | S/C | 2/5 | 0 |
| 14 | 48 | M | anaplastic oligo-dendroglioma | unknown | III | C | 9 | 1 |
| 15 | 1 | M | anaplastic ependymoma | parietal lobe | III | C | 5 | 1 |
| 16 | 14 | F | malignant (anaplastic) astrocytoma | periventricular, occipital | III/IV | S/C | 12/4 | 0 |
| 17 | 69 | M | GBM | temporal lobe | IV | C | 5 | 1 |
| 18 | 4.5 | F | GBM | cerebellopontine | IV | C | 4 | 1 |
| 19 | 1.5 | M | GBM | suprasellar, intraventricular | IV | S/C | 8/10 | 0 |
| 20 | 77 | F | GBM | frontal lobe | IV | C | 6 | 0 |
| 21 | 66 | F | GBM | temporal lobe | IV | C | 11 | 0 |
| 22 | 0.5 | M | medulloblastoma | posterior fossa | IV | C | 6 | 0 |
| 23 | 3 | M | medulloblastoma | posterior fossa | IV | C | 6 | 0 |
| 24 | 44 | M | desmoplastic medulloblastoma | cerebellum | IV | C | 5 | 1 |

GBM = glioblastoma multiforme;
"S" = slice only, "C" = culture only, "S/C" = both slice and culture preparations.

EXAMPLE 17
Experimental Tumors in SCID Mice

Figure 11B:
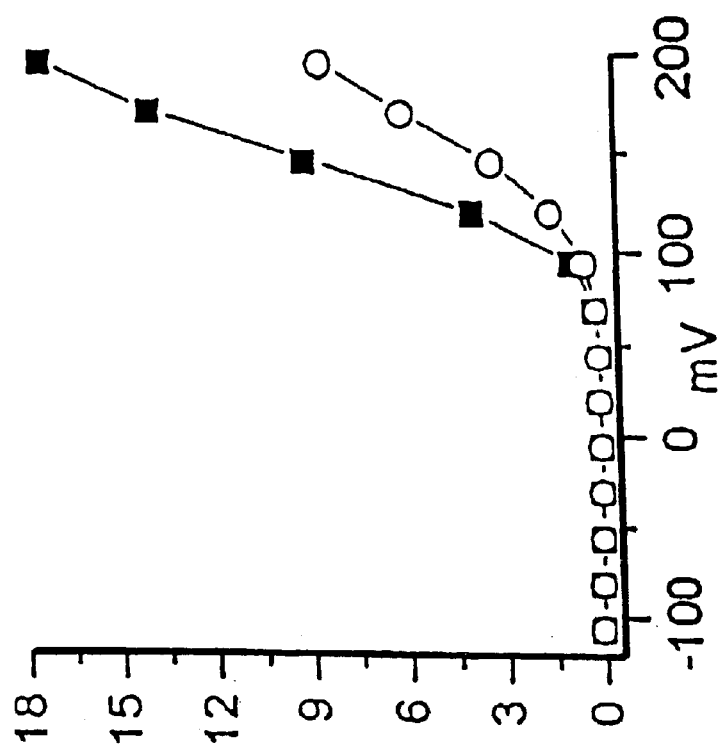
FIGS. 11(a–b) shows the recordings from a xenografted D54MG glioma cell recorded in acute slices in response to depolarizing voltage steps ranging from −105 to 195 mV.
Figure 11A:
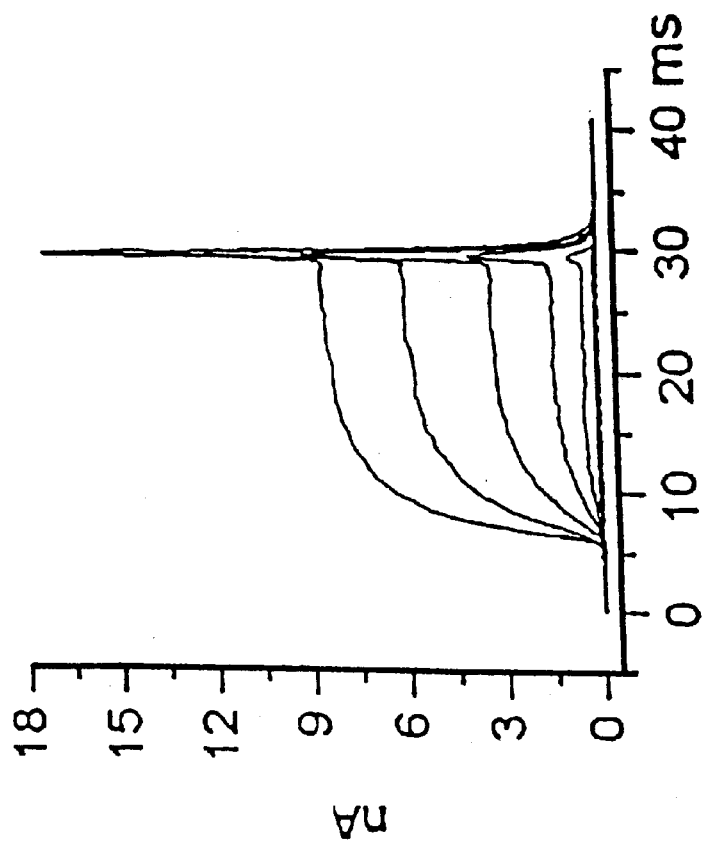
Figure 12:
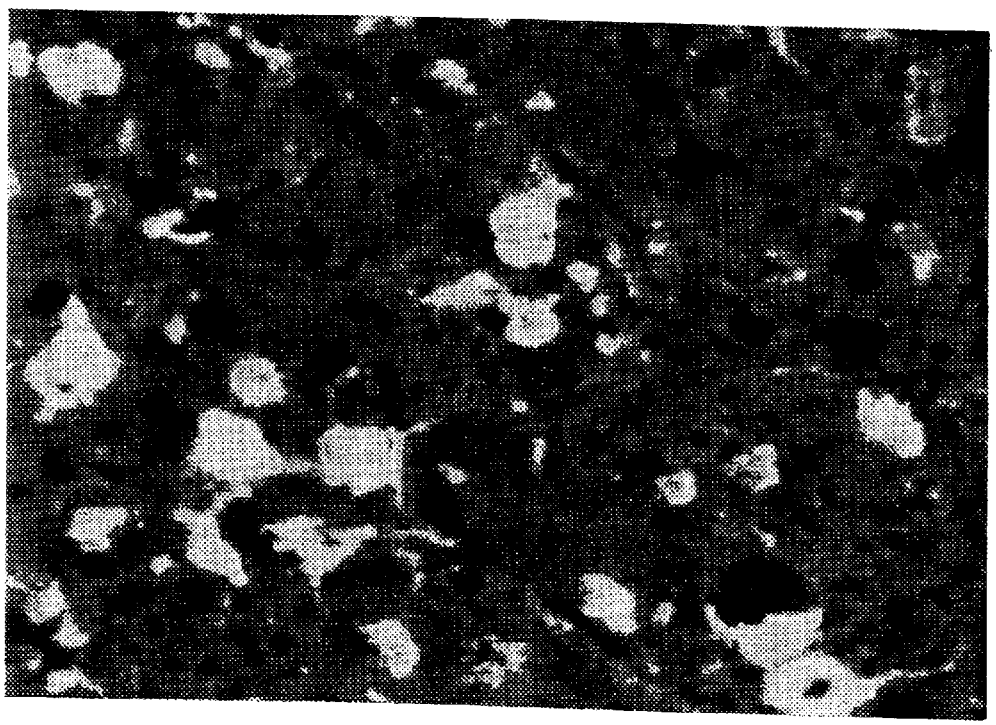
FIG. 12 shows the staining of a 200 μm section through a glioma induced experimentally in a scid mouse. Fluorescent cells are identified by staining with Ctx-GSt recognized by an anti-GST antibody conjugated to FITC. 20× magnification.
Figure 16A:
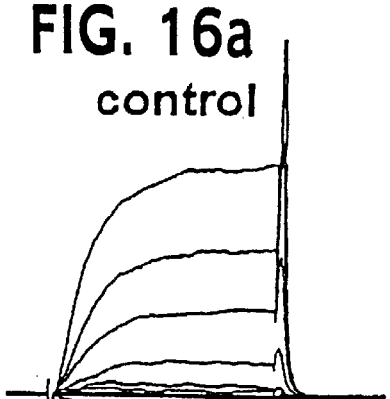
FIGS. 16(a–d) shows a Ctx-GST is an effective blocker of glioma Cl⁻ channels. 600 nM Ctx-GST was applied with bath perfusion and resulted in ∼70% reduction in Cl⁻ currents; GST alone was ineffective.
Figure 16B:
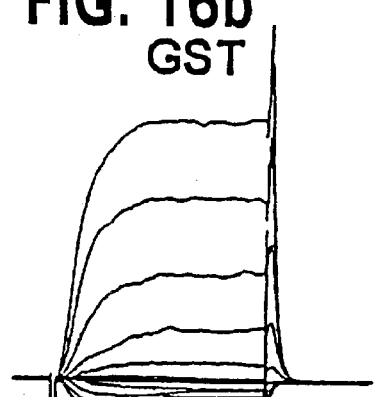
Figure 16C:
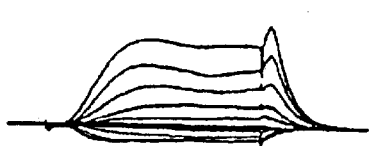
Figure 16D:
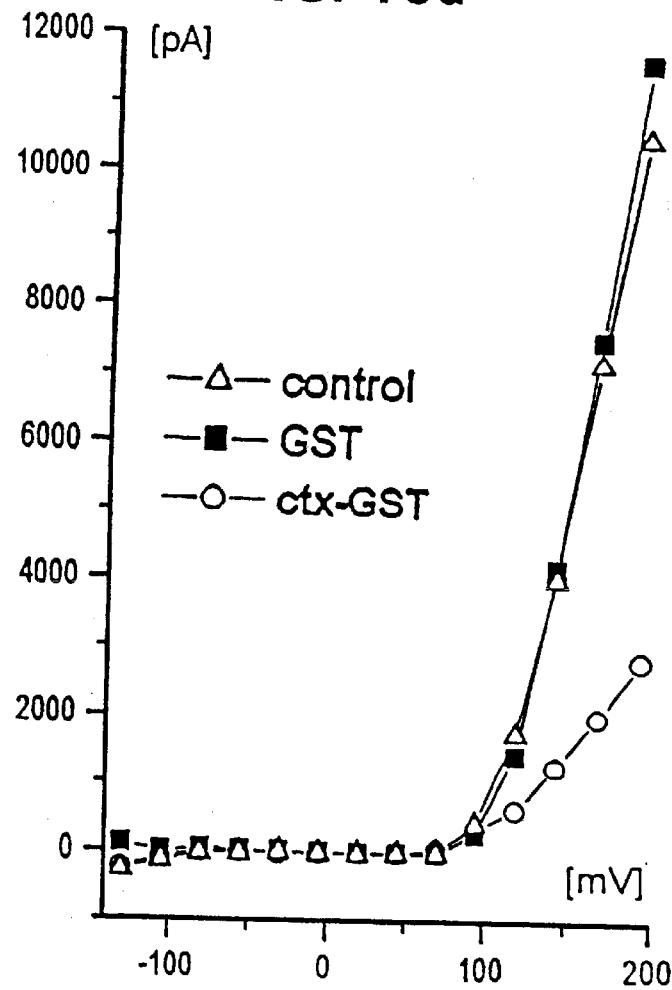

Glioma tumors experimentally induced in SCID mice were also studied by intracranial injection of D54MG glioma cells. This procedure resulted in rapidly growing, invasive brain tumors (Gladson et al. 1995) from which slice preparations were made. Close to 100% of cells in tumor xenografts showed prominent expression of GCC as illustrated by staining of tumor tissue with antibodies that recognize Ctx binding sites (FIG. 12) or electrophysiology (FIG. 11). An example of a representative recording from D54MG cells is shown in FIG. 11. These scid mice were also used to study the biodistribution of Ctx binding sites (therefore GCC channels) using $^{125}$I-Ctx. Therefore, $^{125}$I-Ctx was injected into the cerebrum of a mouse in which a glioma had been induced in the right brain 14 days earlier. Brain and body tissue as well as blood was harvested and $^{125}$I-Ctx levels were determined using a liquid scintillation counter. The resulting counts show the selective accumulation of $^{125}$I-Ctx in the tumor (FIG. 13).

Upon replacement of either intracellular or extracellular potassium ions with $Cs^+$, current amplitude and reversal potential were unchanged. Currents persisted, with altered amplitude, if extracellular chloride was replaced by $Br^-$, $Fl^-$, or $I^-$. Reversal potential shifts indicated that, of these halide ions, $Br^-$ and $I^-$ exhibited greater permeability than either $Cl^-$ or $F^-$.

The current was further characterized pharmacologically by examining the effect of several established $Cl^-$ channel blockers. FIG. 14 shows an 80% decrease in outward current by bath application of 590 nM chlorotoxin to an STTG1 cell. Similar effects were observed with bath or pipette applications of DIDS (100 mM) and DNDS (100 mM) (data not shown). Similar to the work above and based on the pharmacology and ion replacement studies, it was concluded that the outwardly rectifying currents were mediated by an anion. Since under physiological conditions, the current was carried by $Cl^-$, it was referred to as a $Cl^-$ current.

Over 570 cells from primary culture of 6 intracranial tumor resections and 7 cell lines (N>12 cells each) were screened and this $Cl^-$ current was identified in all cells studied. FIG. 3 shows representative examples of voltage-dependent outwardly rectifying anion currents from selected primary cultures and more established cell lines. Cells from primary cultures displayed outward currents that were similar in size, voltage activation, reversal potential, and sensitivity to chlorotoxin as cell lines. Currents were qualitatively similar in all of the 7 cell lines evaluated (U251MG, CH235MG, U373MG, U105MG, D54MG, SK-MG-1, (all glioblastoma multiforme) and STGG1 (anaplastic astrocytoma)). By contrast, such currents were never observed in cell lines derived from other human cancers, such as neuroblastoma, melanoma, breast carcinoma, or rhabdomyosarcoma (See FIG. 15 for representative current traces), nor in rat C6 glioma cells or in primary astrocyte cultures of rat spinal cord or hippocampus (results not shown).

The present invention is the first report of an outwardly-rectifying $Cl^-$ current in human malignant glioma cells. Currents were characteristic of both primary cultures of freshly resected brain tumors and established astrocytoma cell lines. These currents were not present in several extra-glial human tumors such as melanoma, breast, rhabdomyo-sarcoma and neuroblastoma. Chloride currents were characteristic of cells from other preparations, including lymphocytes, submandibular gland, rat myotubes, and sweat gland. However, while the currents were similar in their sensitivity to chloride channel blockers, the $Cl^-$ current in astrocytoma cells exhibits a higher threshold for current activation, had large positive tail currents not previously reported, and could be easily recorded in whole-cell patches. Most interestingly, the present invention demonstrates that this Cl⁻ current is in all tumor cells studied of glial origin but not in normal non-malignant glial cells or in non-glial tumors.

The present invention demonstrates a chloride conductance unique to human astrocytoma and glioblastoma cells which is not present in human tumor cells of extraglial origin. This channel can be blocked physiologically by chlorotoxin, a scorpion venom known to block epithelial chloride channels. The presence of this chloride channel activity presents a diagnostic strategy to differentiate between glial and non-glial tumors.

EXAMPLE 18
Identification and Treatment of Gliomas

Using the teaching of the studies described supra, a person having ordinary skill in this art would readily be able to identify and treat glial-derived neoplastic conditions, i.e., gliomas, astrocytomas, and glioblastomas. For example, chlorotoxin is a 36 amino acid protein naturally derived from *leiurus quinquestriatus* scorpion venom. Using techniques well known in the art, one may prepare recombinant proteins specifically engineered to mimic the binding and action of the native toxin. For example, recombinant chlorotoxin may be synthesized in *E. coli* and by virtue of its high affinity binding to chloride ion channels on the surface of human glial-derived tumors, such recombinant chlorotoxin with an appropriate label are used to identify and isolate glial-derived tumors. Because of the high affinity of the chlorotoxin/channel interaction, a fusion protein such as a primary antibody can be used to stain cells using standard immunohistochemical methods. A GST protein which lacks an insert was also purified for use as a control. An antibody against the GST portion alone can be used as a secondary antibody. In addition, the physiological activity of the fusion protein can be examined by using the GST with no insert as an internal control.

The biological activity of the synthetic chlorotoxin is as effective for chloride ion channel blockade as the native venom toxin. Recombinant techniques are used to synthesize chlorotoxin in *E. coli* using a modified PGEX vector system and the toxin may be linked to various fusion proteins using common restriction sites: GST-chlorotoxin, GST-Ala$_{10}$ linker-chlorotoxin, and GST-Ala$_{20}$ linker-chlorotoxin. These contain no linker, 10 alanine amino acid linker and 20 alanine amino acid linker, respectively. Specifically, three pairs of overlapping oligonucleotides of chlorotoxin sequence deduced from the peptide sequence were synthesized with a HindIII cohesive sequence at the 5' end of the sense oligonucleotide and an EcoRI cohesive sequence following the stop codon at the 3' end of the sense sequence. Each oligonucleotide was phosphorylated by T4 polynucleotide kinase using ATP as a substrate. Nucleotides were annealed by heating and slow cooling. Annealed oligonucleotides were cloned into HindIII/EcoRI site of pGBHE vector (pGCT-1) through ligation followed by transformation into *E. coli* competent cells. Similarly, a 20 amino acid linker was cloned into the BamH1/HindIII site. This amino acid linker has a BgIII site in the middle that makes it possible to cut the BamHI and BgIII in order to create a 10 amino acid linker sequence. The orientation and preservation of the oligonucleotide has been verified within the fusion protein by sequencing methods and that the induction of fusion protein produces the expected size was verified by comparing their molicular weights on a 12% SDS-PAGE gel.

After synthesis of recombinant chlorotoxin, it may be linked to various cytotoxic fusion proteins including glutathione-S-transferase (GST), gelonin, ricin, diptheria toxin, complement proteins and radioligands and other such proteins as are well known in the immunotoxin art. Thus, recombinantly prepared synthetic chlorotoxin linked to a cytotoxic moiety would be useful to specifically target and deliver a toxic substance to glial-derived tumors as a novel therapy. For example, GST-chlorotoxin fusion protein may be prepared as follows. Three fusion proteins, GST alone, GST-chlorotoxin, and GST-Ala$_{20}$ linker-chlorotoxin were affinity purified using a glutothione conjugated agarose bead column and the resulting proteins were verified on a 12% SDS-PAGE gel. More specifically, *E. coli* were transformed with the vector and chlorotoxin insert and were induced to produce the fusion proteins. Resulting proteins were mixed with glutothione agarose beads and left for 15' to optimize absorption. Columns were washed with buffer and the fusion proteins were eluted by competition with free glutathione and collected in small vials. These proteins were then run on a 12% SDS-PAGE gel.

EXAMPLE 19
One Step Conjugation of DTAF (Dichlorotriazinylaminofluorescein) to GST-Ctx Fusion Protein Gluthathione column purified fusion protein Ctx-GST is diluted in 0.2M sodium carbonate (pH 9.0), at 1–2 mg/ml. DTAF (Calbiochem) is diluted in 1.0 M sodium carbonate (pH 9.0) at 2.5 mg/ml. DTAF is mixed gently with the diluted Ctx-GST, by adding 25 mg DTAF per milligram of Ctx-GST. Mixing continues at room temperature for 10 minutes, after which NH$_4$Cl is added at a final concentration of 50 mM and glycerol up to 5% final volume (optional, xylene cylanol 0.1% is added to serve as indicator dye for the unbound material). The solution is placed at 4° C. for 2–4 hours with gentle agitation. After mixing, the unbound dye is separated by gel size filtration (G-Sephadex column, with exclusion limit between 30,000–50,000 prepared according to the manufacturer's instructions (Pharmacia)). The conjugated Ctx-GST-DTAF elutes first, and its color is easily distinguished under room light. Protein content is then determined, and the fluorescent conjugate is stored in a light proof-container at 4° C., until ready to use for direct immunofluorescence labeling of cells or slices as described below.

EXAMPLE 20
Chlorotoxin Binding Identified by Immunohistochemistry

GST-chlorotoxin (Ctx-GST) or Ctx-GST-DTAF are used to identify toxin binding sites. Ctx-GST is biologically active, binds to and blocks Cl⁻ channels with similar affinity as the venom toxin. Ctx-GST are recognized immunohistochemically by an antibody to GST (Chemicon) conjugated to either rhodamine or FITC, and binding are assayed under a fluorescence microscope. Alternatively, a single step fluorescence staining procedure are used utilizing Ctx-GST-DAFT (above), a fluorescent form of the Ctx-GST. The DTAF label can be visualized by direct immunofluoresence using standard FITC filters. The Ctx-GST-DTAF staining has the advantage that cross-reactivity with native GST does not pose a problem.

Antibodies to the chloride ion channels in glial derived tumors may be prepared as follows. Polyclonal antisera are generated by injecting fusion proteins created between the glutathione-S-transferase and the chlorotoxin insert into mice or rabbits. Mice are immunized with 0.5 ml of a 1:1 emulsion of 1 mg/ml purified fusion protein in Freund's complete adjuvant and subsequently with two additional injections after 14 and 28 days in Freund's incomplete adjuvant. The mouse and rabbit antibodies are purified from the antisera using the GST fusion protein immobilized on nitrocellulose filters. The antibodies are then examined for binding specificity in various tissues.

Figure 17:
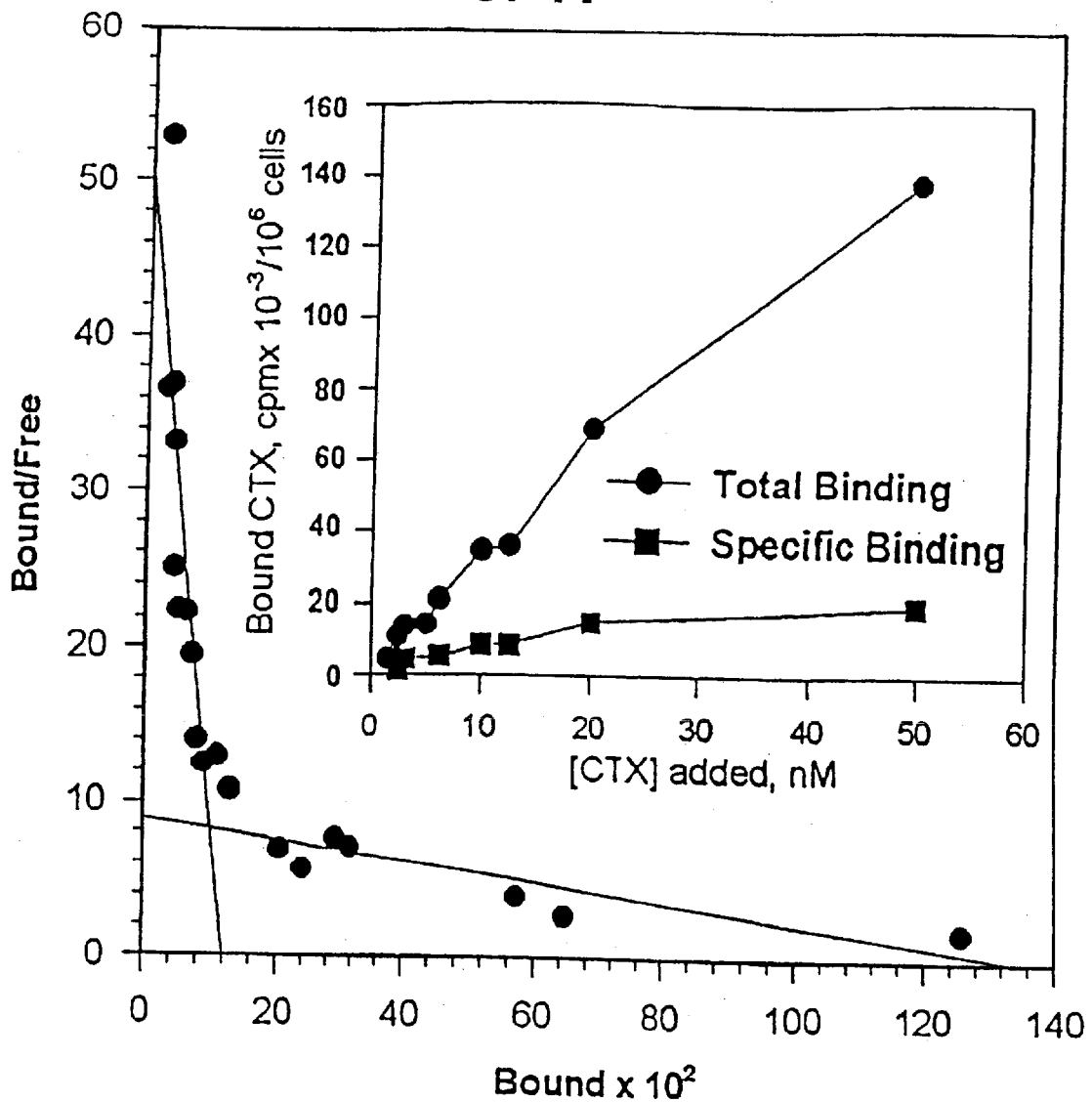
FIG. 17 shows that binding of $^{125}$[I]-CTX to D54MG glioma cells. $^{125}$[I]-CTX was added in duplicate in 400 mL with or without a 100-fold molar excess of unlabeled Ctx from the same source. After 60 min at room temperature, cell monolayers were rinsed 3 times with PBS and cells were harvested for assessment of cell-associated radioactivity. Four wells in each plate were harvested with trypsin-EDTA and cell number was established by trypan blue exclusion. (Note that not all data points used for the Scatchard analysis were plotted in the inset).

EXAMPLE 21
Glioma Cells Bind $^{125}$[I]-Chlorotoxin with High Affinity and Selectivity To utilize Ctx-like molecules to selectively target glioma cells, it is essential to establish the selective high affinity binding of Ctx to glioma cells. Therefore, binding affinity was determined using ($^{125}$[I]-Ctx) radiolabeled with $^{125}$[I]-sodium iodide by the chloramine-T method. Saturated binding was achieved in D54MG glioblastoma cells at concentrations >15 nM (FIG. 17, inset). Scatchard analysis of these data indicates two binding sites with estimated binding affinity values (Kd) of 4.2 nM and 660 nM. The latter value is in good agreement with the electrophysiologically determined $IC_{50}$ of ~950 nM. D54MG cells contain approximately 1,300 high affinity Ctx binding sites and 13,300 low affinity binding sites per cell. By contrast, no specific Ctx binding was observed in normal human glial cells nor in mixed brain cell cultures (not shown), suggesting that in brain, Ctx binding is glioma specific. This observations suggest that Ctx with radioactive moieties can be used to treat gliomas. The molecule would selectively bind to gliomas and expose cells to high levels of radiation. $^{125}$I-Ctx or 131I-Ctx are candidates for this purpose.

EXAMPLE 22
Immunohistochemical Detection of Chlorotoxin

Figure 18:
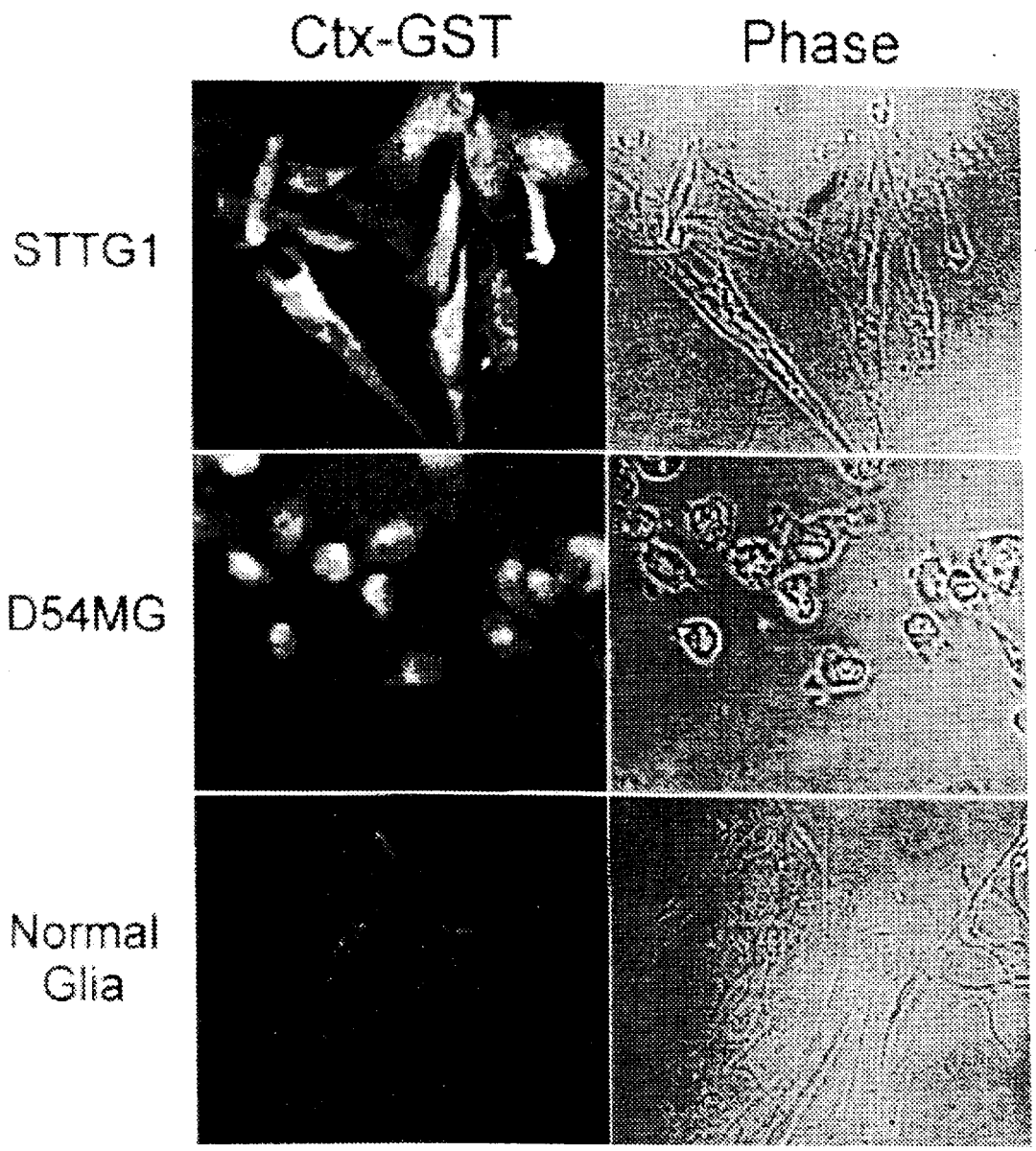
FIG. 18 shows the immunohistochemical staining of two glioma cell lines as compared to normal human glia. Cells were labeled with the recombinant chlorotoxin-GST fusion protein (Ctx-GST) and binding of Ctx-GST was visualized by an anti-GST antibody coupled to FITC.

While electrophysiology is the perfect tool to detect channel activity, it cannot show the presence of inactive or quiescent channels. Other means to detect GCC channels are thus desirable and are particularly important for use of GCC as a diagnostic marker. Chlorotoxin binding can be detected immunohistochemically using several approaches. First, cells can be labeled with Ctx-GST, the fusion protein that also inhibits GCC currents (see above, FIG. 16). This fusion protein can be detected by a FITC-conjugated antibody to GST, although numerous other detection procedures would be possible. As shown in FIG. 18, this approach selectively labels astrocytoma and glioblastoma derived cell lines such as STTG1 or D54MG, but fails to label normal human glial cells. These studies, obtained in vitro, demonstrate the ability to use this approach for the detection of Ctx binding sites and can be used as a diagnostic marker for gliomas in human biopsies. Secondly, chlorotoxin can be labeled using DTAF as Ctx-DTAF. This procedures resulted in a directly fluorescent Ctx-molecule that selectively labels gliomas. Similarly, chlorotoxin can be directly conjugated with biotin as Ctx-biotin. This allows binding to be identified using a reaction with avidin and subsequent recognition by antibodies or the reaction product. This approach was likewise successful in selectively labeling glioma and meningioma cells.

EXAMPLE 23
Immunotoxins Targeted to the Ctx Binding Site can Specifically Kill Glioma Cells In Vitro Since Ctx-GST selectively labels glioma cells, one may target and eliminate tumor cells by conjugating Ctx-GST to a known immunotoxin, e.g., saporin (Benatti et al. 1989; Battelli et al. 1990; Fordham-Skelton et al. 1990; Tecce et al. 1991; Fordham-Skelton et al. 1991). Such chimeric proteins can be made by fusing Ctx (the targeting moiety) with saporin (the toxin moiety).

Figures 19A, 19B, 19C, 19D:
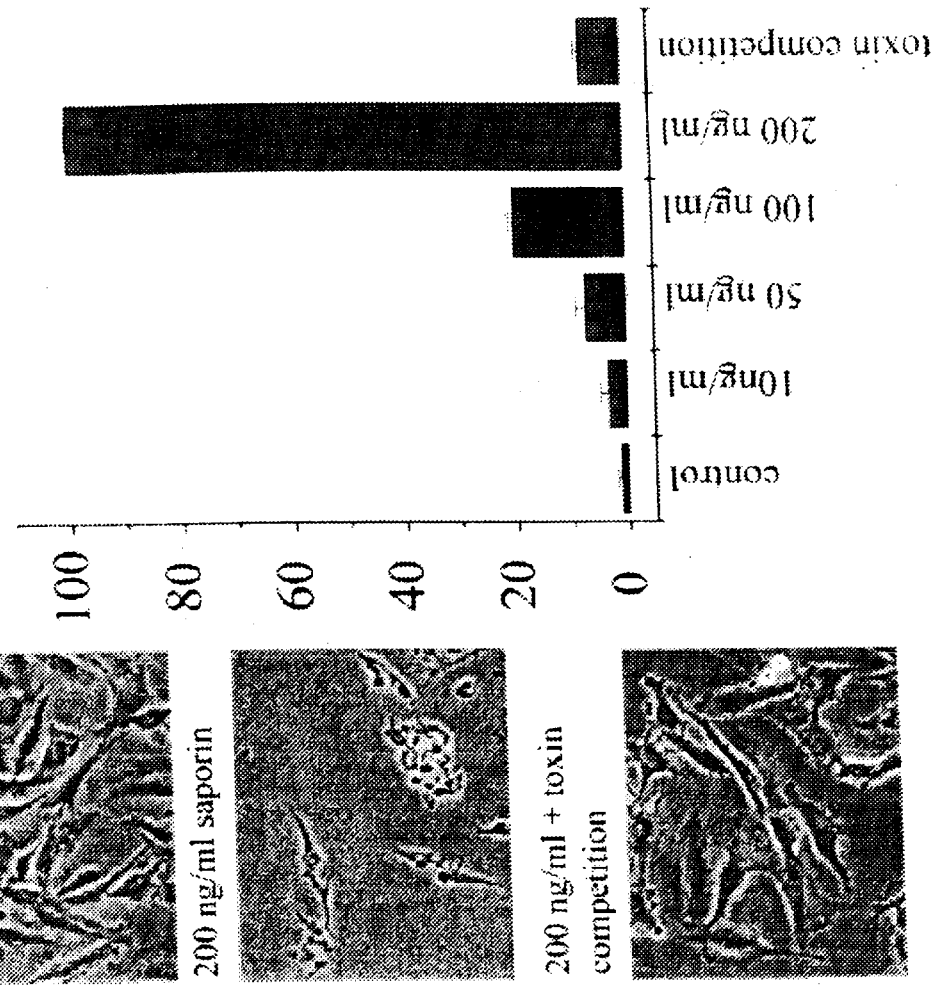
FIGS. 19(a–q) show the glioma cells were exposed to 600 nM Ctx-GST followed by a mouse aGST and a goat anti-mouse antibody conjugated to saporin. Cell death increased with increasing saporin concentrations (right) and could be largely prevented by pre-treatment of cultures with 6 μM native chlorotoxin (bottom left).

Using this approach, glioma cells were first treated with Ctx-GST, followed by a mouse anti-GST monoclonal antibody and lastly a goat anti-mouse antibody conjugated to saporin. This last step confers immunotoxicity on the "primary" (in this case, Ctx-GST) antibody and resulted in significant and specific killing of glioma cells (FIG. 19). Normal nontumor human astrocytes were not influenced by treatment with the saporin conjugate and either antibody alone failed to reduce cell numbers or to reduce protein or DNA synthesis, as assayed by $^3$H-leucine and $^3$H-thymidine, respectively.

EXAMPLE 24
Molecular Identity of GCC

Figure 20:
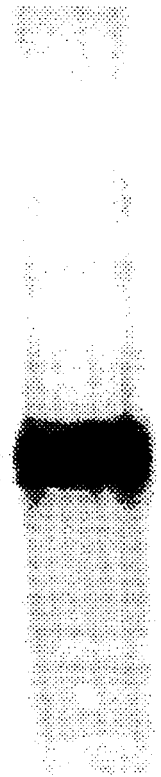
FIG. 20 shows a western blot of U54MG membranes after immunpercipitation with either ClC5 antibodies or chlorotoxin (Ctx). Blots were probed with ClC5.

Western blots from glioma membranes were obtained and probed with chlorotoxin-biotin. With this approach, a ~70 kD protein band (FIG. 20) was identified. This band was also recognized by an antibody specifically generated to CLC-5, a chloride channel expressed in the kidney (Sakamoto et al. 1996; Steinmeyer et al. 1995). (This antibody was kindly provided by Drs. Jentsch and Guenther). Immunopercipitation with CLC-5 antibodies and subsequent probing with Ctx-biotin identified the same 70 kD band suggesting that GCC must have a high homology to CLC-5.

The following reference were cited herein:
1. Bakhramov, A., et al., *Exp. Physiol.* 80: 373–389, (1995).
2. Becq, F., et al., *Pflugers Archiv—European Journal of Physiology* 420: 46–53, (1992).
3. Blatz, A. L., et al., *Biophys. J.* 43: 237–241, (1983).
4. Brismar, T., et al., *Brain Res.* 480: 249–258, (1989).
5. Chiu, S. Y., et al., *J. Physiol. (London)* 408: 199–222, (1989).
6. Dani, J. A., et al., *J. Gen. Phys.* 81: 255–281, (1983).
7. Deane, K. H., et al., *Eur. J. Immunol.* 22: 1165–1171, (1992).
8. DeBin, J. A., et al., *Am. J. Physiol.* 264: C361–9, (1993).
9. Evans, M. G., et al., *Journal of Physiology* 378: 437–460, (1986).
10. Frizzell, R. A., et al., Chloride Channels in Epithelial Cells. In: *Current Topics in Membranes and Transport*, AnonymousAcademic Press, p. 247–282, (1990).
11. Garber, S. S., *J. Mem. Biol.* 127: 49–56, (1992).
12. Giraldez, F., et al., *Journal of Physiology* 416: 517–537, (1989).
13. Gray, M. A., et al., *Am. J. Physiol.* 257: Pt 1):C240–51, (1989).
14. Gray, P., et al., *Proc. Roy. Soc. Lond.* 228: 267–288, (1986).
15. Grissmer, S., et al., *J. Gen. Phys.* 102: 601–630, (1993).
16. Holevinsky, K. O., et al., *J. Mem. Biol.* 140: 13–30, (1994).
17. Huang, Y., et al., *J. Biol. Chem.* 269: 31183–31189, (1994).
18. Inoue, I., *J. Gen. Phys.* 85: 519–537, (1985).
19. Ishikawa, T., et al., *Pflugers Arch.* 427: 203–209, (1994).
20. Jalonen, T., *Glia* 9: 227–237, (1993).
21. Kleihues, P., et al., *Brain Pathology* 3: 255–268, (1993).
22. Korr, H. Proliferation and cell cycle parameters of astrocytes. In: *Astrocytes*, by S. Fedoroff ed. Acad. Press, p. 77–127, (1986).
23. Krouse, M. E., et al., *Am. J. Physiol.* 257: C129–40, (1989).
24. Kunzelmann, K., et al., *Pflugers Arch- Euro. J. of Phys.* 415: 172–182, (1989).
25. Li, M., et al., *Am. J. Physiol.* 259: Pt 1):C295–301, (1990).
26. Linskey, M. E., et al., *Neurosurgery* 36: 1–22, (1995).
27. Nelson, D. J., et al., *J. Mem. Biol.* 80: 81–89, (1984).
28. Nilius, B., et al., *J. of Physiology—London* 445: 537–548, (1992).

29. Pappas, C. A., et al., *Neuroreport* 6: 193–196, (1994).
30. Pappone, P. A., et al., *Am. J. Physiol.* 264: C1014–C1019, (1993).
31. Pollard, C. E., et al., *J. Mem. Biol.* 124: 275–284, (1991).
32. Puro, D. G., et al., *Invest. Ophatl. & Vis. Sci.* 30: 521–529, (1989).
33. Quasthoff, S., et al., *Glia* 5: 17–24, 1992.
34. Robinson, R., et al., Thermodynamics of mixed electrolytes. In: *Electrolyte solutions*. London: Butterworths, 1959, p. 432–549.
35. Schlichter, L., *Can. J. Physiol. & Pharmacol.* 70: 247–258, (1992).
36. Schwarze, W., et al., *Pflugers Archiv—European Journal of Physiology* 402: 281–291, (1984).
37. Sontheimer, H., *Glia* 11: 156–172, (1994).
38. Sontheimer, H., et al., *J. Neurophysiol.* 65: 3–19, (1991).
39. Ullrich, N., et al., *Neuroreport* (1995).
40. Wilson, G. F., et al., *J. Physiol.* (*London*) 470: 501–520, (1993).
41. Woodfork, K. A., et al., *J. Cell. Physiol.* 162: 163–171, (1995).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A pharmaceutical composition comprising chlorotoxin wherein the pharmaceutical composition is suitable for use in humans.

2. The composition of claim 1 wherein the chlorotoxin is selected from the group consisting of recombinant chlorotoxin, synthetic chlorotoxin and native chlorotoxin.

3. The composition of claim 1 wherein the chlorotoxin is recombinant chlorotoxin.

4. The composition of claim 1 wherein the chlorotoxin is labeled.

5. The composition of claim 4 wherein the chlorotoxin label is a radiolabel.

6. The composition of claim 5 wherein the chlorotoxin radiolabel is selected from the group consisting of $^{131}$I and $^{125}$I.

7. The composition of claim 4 wherein the chlorotoxin label is a fluorescent moiety.

8. A pharmaceutical composition comprising a pharmacologically effective dose of chlorotoxin and a cytotoxic moiety that is effective to treat an individual having a glioma or meningioma.

9. A pharmaceutical composition comprising a pharmacologically effective dose of chlorotoxin and a cytotoxic moiety that is effective to suppress the growth of tumor cells which are glial in origin.

* * * * *